(12) United States Patent
Fujino et al.

(10) Patent No.: US 10,101,348 B2
(45) Date of Patent: Oct. 16, 2018

(54) SAMPLE ANALYZER

(71) Applicant: Sysmex Corporation, Kobe-shi, Hyogo (JP)

(72) Inventors: Hiroyuki Fujino, Kobe (JP); Kyozo Fujita, Kobe (JP); Mitsuyo Ito, Kobe (JP)

(73) Assignee: Sysmex Corporation, Kobe-Shi, Hyogo (JP)

( * ) Notice: Subject to any disclaimer, the term of this patent is extended or adjusted under 35 U.S.C. 154(b) by 107 days.

(21) Appl. No.: 15/171,532

(22) Filed: Jun. 2, 2016

(65) Prior Publication Data
US 2016/0274136 A1 Sep. 22, 2016

Related U.S. Application Data

(63) Continuation of application No. 11/893,926, filed on Aug. 17, 2007, now Pat. No. 9,372,199.

(30) Foreign Application Priority Data

Aug. 18, 2006 (JP) .................................. 2006-222850
Aug. 29, 2006 (JP) .................................. 2006-231591

(51) Int. Cl.
*G01N 1/00* (2006.01)
*G01N 35/00* (2006.01)
(Continued)

(52) U.S. Cl.
CPC . *G01N 35/00732* (2013.01); *G01N 35/00663* (2013.01); *G01N 35/025* (2013.01);
(Continued)

(58) Field of Classification Search
CPC ....................................................... G01N 1/00
See application file for complete search history.

(56) References Cited

U.S. PATENT DOCUMENTS 5,316,726 A 5/1994 Babson et al.
6,090,630 A 7/2000 Koakutsu et al.
(Continued)

FOREIGN PATENT DOCUMENTS

JP 10-142230 A 5/1998
JP 2000-346851 A 12/2000
(Continued)

*Primary Examiner* — Jyoti Nagpaul
(74) *Attorney, Agent, or Firm* — Brinks Gilson & Lione

(57) ABSTRACT

The sample analyzer includes: a reagent arranging section for arranging a plurality of reagents; an analyzing section for analyzing a measurement sample prepared by mixing a sample and the reagent arranged on the reagent arranging section; a display device; an input device; and a display control section for displaying a reagent arrangement displaying region for displaying a plurality of reagent marks inscribed with a reagent name respectively on the display device, wherein the each reagent mark is displayed in a manner selectable by the input device, wherein arrangement of the each reagent mark on the reagent arrangement displaying region corresponds to arrangement of the each reagent on the reagent arranging section, wherein the display control section displays detailed information related to the reagent corresponding to the reagent mark selected by the input device on the display device.

20 Claims, 27 Drawing Sheets

(51) Int. Cl.
*G01N 35/02* (2006.01)
*B01L 9/06* (2006.01)

(52) U.S. Cl.
CPC ...... *B01L 9/06* (2013.01); *G01N 2035/00673* (2013.01); *G01N 2035/00891* (2013.01)

(56) References Cited

U.S. PATENT DOCUMENTS

| | | |
|---|---|---|
| 6,349,264 B1 | 2/2002 | Rhett et al. |
| 7,384,601 B2 | 6/2008 | Matsubara et al. |
| 7,390,460 B2 | 6/2008 | Osawa et al. |
| 7,931,863 B2 * | 4/2011 | Kitagawa ......... G01N 35/00663 422/63 |
| 2001/0051952 A1 | 12/2001 | Nakazato |
| 2002/0116132 A1 | 8/2002 | Rhett et al. |
| 2005/0013736 A1 | 1/2005 | McKeever |
| 2006/0173575 A1 | 8/2006 | Lefebvre et al. |
| 2008/0014118 A1 | 1/2008 | Kitagawa et al. |

FOREIGN PATENT DOCUMENTS

| | | |
|---|---|---|
| JP | 2001-133462 | 5/2001 |
| JP | 2001-281258 A | 10/2001 |
| JP | 2003-066049 A | 3/2003 |
| JP | 2004-028932 A | 1/2004 |

* cited by examiner

SAMPLE ANALYZER

PRIORITY

This application claims priority as a Continuation to U.S. application Ser. No. 11/893,926, entitled "Sample Analyzer," filed on Aug. 17, 2007, now U.S. Pat. No. 9,372,199, which claims priority under 35 U.S.C. § 119 to Japanese Patent Application No. 2006-222850 filed Aug. 18, 2006 and Japanese Patent Application No. 2006-231591 filed Aug. 29, 2006, the entire disclosures of each of which are hereby incorporated by reference.

FIELD OF THE INVENTION

The present invention relates to a sample analyzer.

BACKGROUND OF THE INVENTION

A sample analyzer equipped with a display screen for displaying detailed information of the arranged reagent is conventionally known (see e.g., Japanese Laid-Open Patent Publication No. 2001-133462). In such sample analyzer disclosed in Japanese Laid-Open Patent Publication No. 2001-133462, when the reagent is specified on the display screen, the state of the specified reagent is confirmed, and the confirmation result (detailed information) is displayed on the display screen. Furthermore, in the sample analyzer disclosed in Japanese Laid-Open Patent Publication No. 2001-133462, a reagent stocker is displayed on the display screen on a frame format view, and the detailed information of each reagent bottle installed in the reagent stocker such as item name, remaining amount (number of times), lot number or serial number, and the like can be confirmed on the display screen.

Recently, the number of reagents to be arranged in the sample analyzer is increasing to a few dozens to about a hundred due to increase in the number of measurement items and improvement on the processing speed of the sample analyzer described above. It is thus desired to be able to easily confirm the detailed information such as arrangement, item name, lot number, or the like of the reagent on the display screen.

Although the sample analyzer disclosed in Japanese Laid-Open Patent Publication No. 2001-133462 is configured to display the detailed information of all the arranged reagents, the detailed information of all the arranged reagents are difficult to display when a great number of reagents are arranged since the space of the displaying region of the display screen is limited.

SUMMARY OF THE INVENTION

The scope of the present invention is defined solely by the appended claims, and is not affected to any degree by the statements within this summary.

The first aspect of the present invention relates to a sample analyzer comprising: a reagent arranging section for arranging a plurality of reagents; an analyzing section for analyzing a measurement sample prepared by mixing a sample and the reagent arranged on the reagent arranging section; a display device; an input device; and a display control section for displaying a reagent arrangement displaying region for displaying a plurality of reagent marks inscribed with a reagent name respectively on the display device, wherein the each reagent mark is displayed in a manner selectable by the input device, wherein arrangement of the each reagent mark on the reagent arrangement displaying region corresponds to arrangement of the each reagent on the reagent arranging section, wherein the display control section displays detailed information related to the reagent corresponding to the reagent mark selected by the input device on the display device.

The second aspect of the present invention relates to a sample analyzer comprising: a reagent arranging section for arranging a plurality of reagents; an analyzing section for analyzing a measurement sample prepared by mixing a sample and the reagent arranged on the reagent arranging section; a display device; an input device; and a display control section for displaying reagent managing screen including a first region for displaying a plurality of reagent marks inscribed with reagent names respectively and a second region for displaying a replacement mark for replacing the reagent arranged on the reagent arranging section, wherein the each reagent mark and the replacement mark are displayed in a manner selectable by the input device, wherein arrangement of the each reagent mark on the first region corresponds to arrangement of the each reagent on the reagent arranging section, wherein when one of the reagent marks is selected by the input device and the replacement mark is selected by the input device, the reagent arranging section performs a reagent replacement operation for replace the reagent corresponding to the selected regent mark.

The third aspect of the present invention relates to a sample analyzer comprising: a reagent arranging section in which a plurality of reagents are capable of being arranged in a movable manner; an analyzing section for analyzing a measurement sample prepared by mixing a sample and the reagent arranged on the reagent arranging section; a display device; an input device; and a display control section for displaying reagent managing screen including a reagent arrangement displaying region for displaying a plurality of reagent marks inscribed with reagent names respectively, wherein the each reagent mark and the replacement mark are displayed in a manner selectable by the input device, wherein arrangement of the each reagent mark on the reagent arrangement displaying region corresponds to arrangement of the each reagent on the reagent arranging section, wherein the display control section controls the display device to display the reagent mark corresponding to the reagent which has a problem to be used for analysis in a manner distinguishable from the reagent mark corresponding to the reagent which does not have a problem to be used for analysis.

DESCRIPTION OF THE PREFERRED EMBODIMENTS

Embodiments embodying the present invention will now be described based on the drawings.

Figure 15:
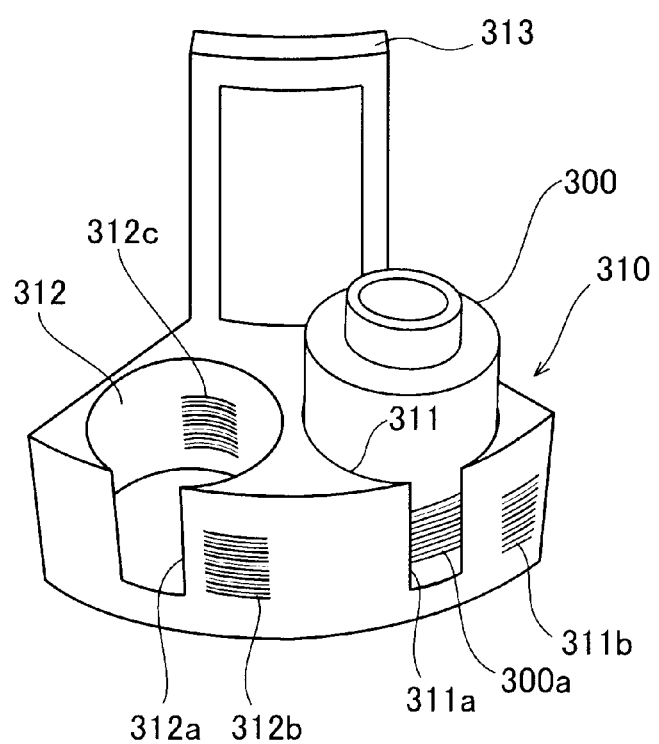
FIG. 15 is a perspective view showing a state in which a reagent container is held in the first reagent container rack shown in FIG. 13.
Figure 16:
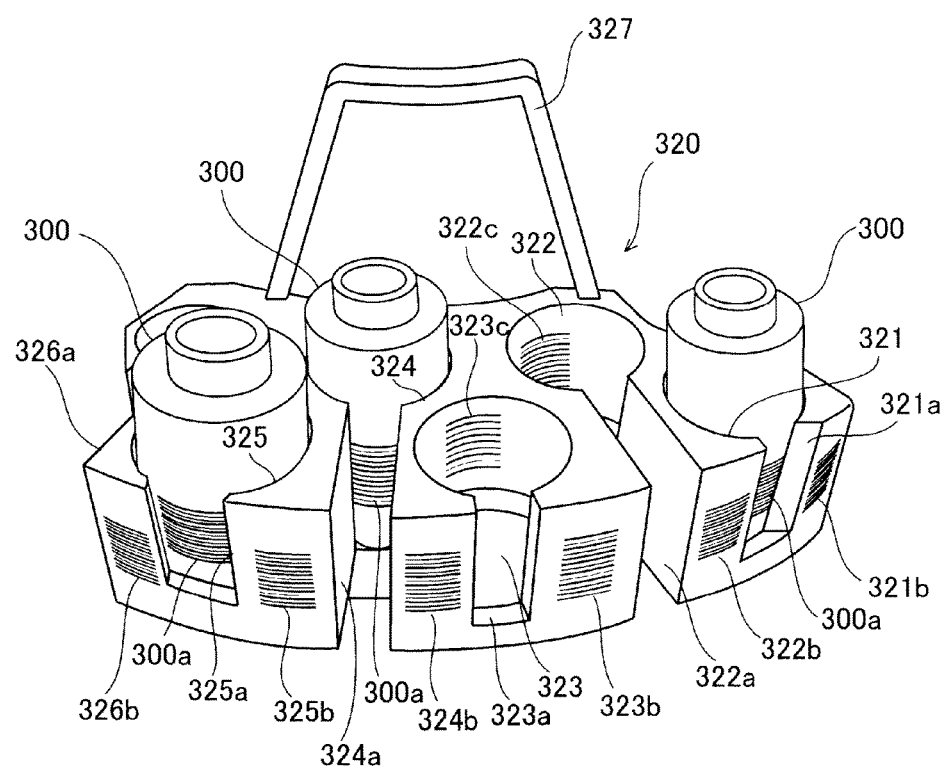
FIG. 16 is a perspective view showing a state in which the reagent container is held in the second reagent container rack shown in FIG. 14.
Figure 17:
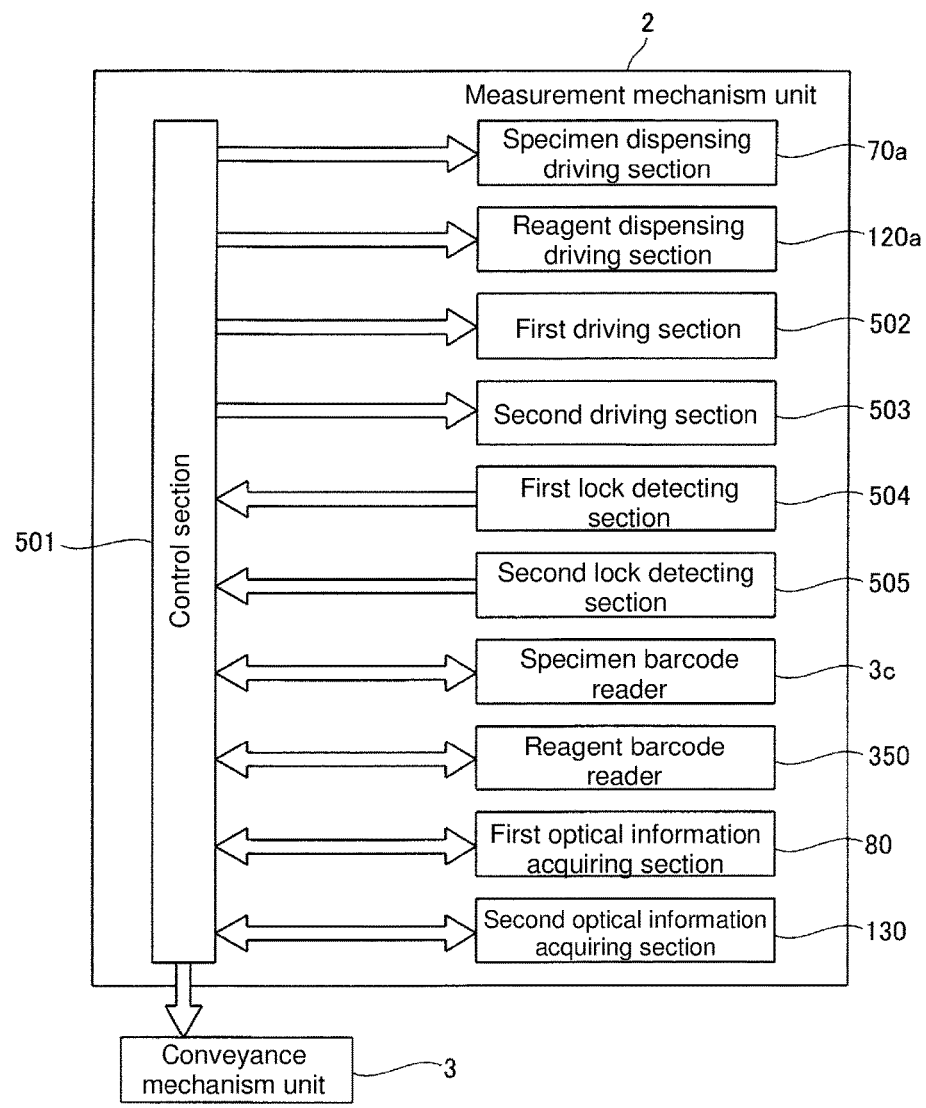
FIG. 17 is a block diagram of the sample analyzer according to one embodiment of the present invention.
Figure 18:
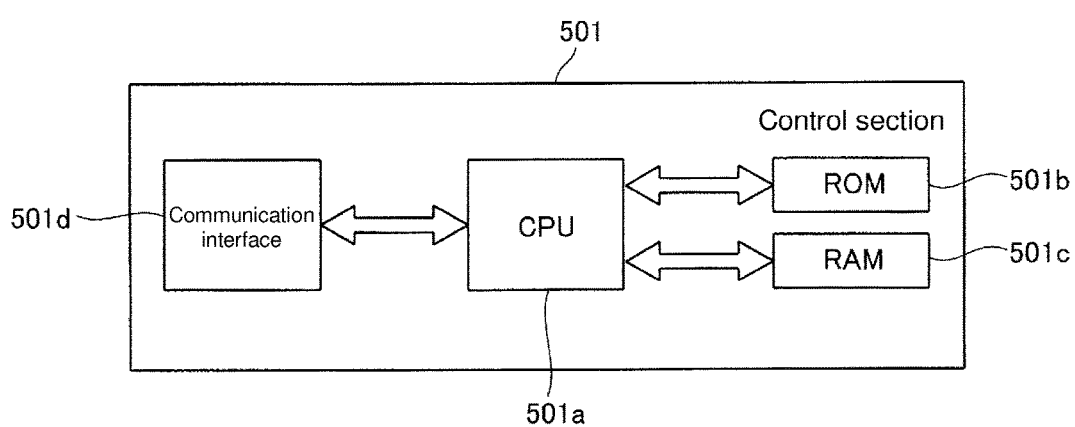
FIG. 18 is a block diagram of a control section of the measurement mechanism unit of the sample analyzer according to the one embodiment of the present invention.

FIGS. 1 to 5 are views showing an overall configuration of a sample analyzer according to one embodiment of the present invention. FIG. 6 is a view describing a control device of a sample analyzer according to the one embodiment of the present invention. FIGS. 7 to 12 are views describing a screen displayed on a display device of the sample analyzer according to the one embodiment of the present invention. FIGS. 13 to 16 are perspective views showing a reagent container rack and a reagent container of the sample analyzer according to the one embodiment of the present invention. FIGS. 17 and 18 are block diagrams describing the details of the sample analyzer according to the one embodiment of the present invention. First, the structure of the sample analyzer 1 according to the one embodiment of the present invention will be described with reference to FIGS. 1 to 18.

The sample analyzer 1 according to the one embodiment of the present invention is a device for analyzing the amount or degree of activity of a specific substance related to coagulation and fibrolytic function of the blood by optically measuring the same, and uses blood plasma for the specimen. The optical measurement (main measurement) of the specimen is performed in the sample analyzer 1 according to the one embodiment using coagulation time method, synthetic substrate method, and immunoturbidimetric method. The coagulation time method used in the present embodiment is a measuring method of detecting the coagulating process of the specimen as change in transmitted light. The measurement items include PT (prothrombin time), APTT (activated partial thromboplastin time), Fbg (Fibrinogen content) or the like. The measurement item of the synthetic substrate method includes ATIII, and the measurement item of the immunoturbidimetric method includes D dimer, FDP or the like.

Figure 1:
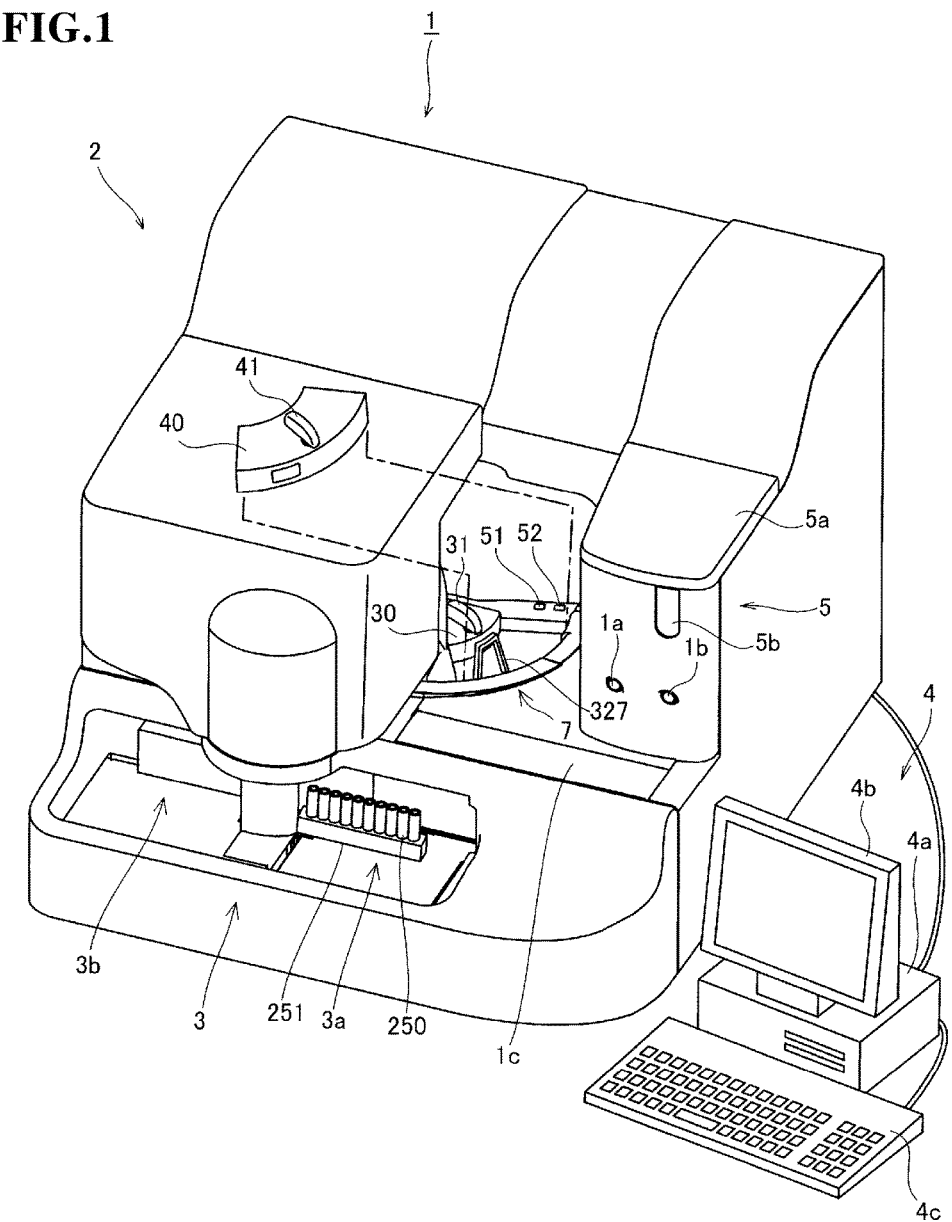
FIG. 1 is a perspective view showing an overall configuration of a sample analyzer according to one embodiment of the present invention.
Figure 2:
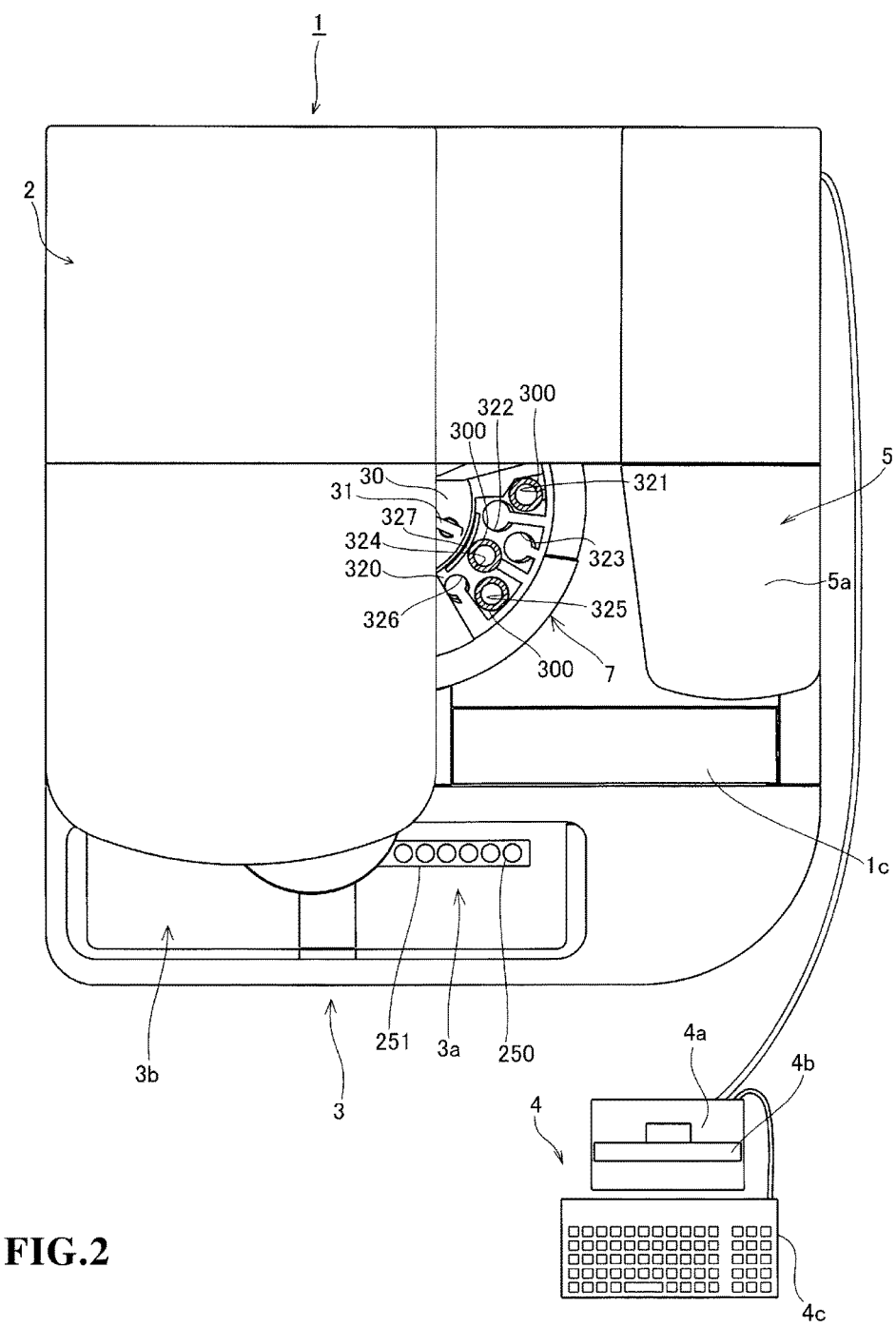
FIG. 2 is a plan view of the sample analyzer shown in FIG. 1.

As shown in FIGS. 1 and 2, the sample analyzer 1 is configured by a measurement mechanism unit 2, a specimen conveyance mechanism unit 3 arranged on the front face side of the measurement mechanism unit 2, and a control device 4 electrically connected to the measurement mechanism unit 2. A cuvette placing section 5 for placing the cuvette 200 (see FIG. 4), which is the container of the specimen when performing the measurement, is arranged in the measurement mechanism unit 2. An openable/closable lid 5a and a window 5b through which the interior of the cuvette placing section 5 can be seen are formed in the cuvette placing section 5. An urgent stop button 1a and a measurement start button 1b are arranged on the front face side of the cuvette placing section 5. The lid 5a (see FIG. 1) is provided to place the cuvette 200 into a first hopper 161a (see FIG. 4) of a cuvette supply mechanism section 160, to be hereinafter described. The user is able to see the remaining amount of the cuvette 200 stored in the first hopper 161a (see FIG. 4) through the window 5b. The urgent stop button 1a (see FIG. 1) has a function of stopping the measurement in time of urgency. The measurement start button 1b (see FIG. 1b) has a function of starting the measurement when pushed. The user thus can immediately start the measurement after placing the cuvette 200. The measurement can also be started or stopped through operation of the control device 4.

As shown in FIGS. 1 and 2, the control device 4 consists of a personal computer 401 (PC), and includes a control section 4a, a display device 4b and a keyboard 4c. The control section 4a is adapted to transmit an operation start signal of the measurement mechanism unit 2 to a control section 501 of the measurement mechanism unit 2, to be hereinafter described, and analyze optical information of the specimen obtained by the measurement mechanism unit 2. The control section 4a is made up of CPU, ROM, RAM, or the like. The display device 4b is provided to display information associated with interference substance (hemoglobin, milky fluid (fat), and bilirubin) present in the specimen, as well as the result of analysis obtained by the control section 4a.

The configuration of the control device 4 will now be described in detail. As shown in FIG. 6, the control section 4a is mainly configured by a CPU 401a, a ROM 401b, a RAM 401c, a hard disc 401d, a read-out device 401e, an input/output interface 401f, a communication interface 401g, and an image output interface 401h. The CPU 401a, the ROM 401b, the RAM 401c, the hard disc 401d, the read-out device 401e, the input/output interface 401f, the communication interface 401g, and the image output interface 401h are connected by a bus 401i.

The CPU 401a executes computer programs stored in the ROM 401b and the computer programs loaded in the RAM 401c. The computer 401 serves as the control device 4 when the CPU 401a executes the application program 404a, as hereinafter described.

The ROM 401b is configured by mask ROM, PROM, EPROM, EEPROM, and the like, and is recorded with computer programs to be executed by the CPU 401a, data used for the same, and the like.

The RAM 401c is configured by SRAM, DRAM, and the like. The RAM 401c is used to read out the computer programs recorded on the ROM 401b and the hard disc 401d. The RAM 401c is used as a work region of the CPU 401a when executing the computer programs.

The hard disc 401d is installed with various computer programs to be executed by the CPU 401a such as operating system and application program, as well as data used in executing the computer program. The application program 404a for calculating the presence and concentration of the interference substance according to the present invention is also installed in the hard disc 401d. In the present embodiment, a table of a reagent master, a reagent lot master, and a container master to be hereinafter described is stored in the hard disc 401d.

The read-out device 401e is configured by flexible disc drive, CD-ROM drive, DVD-ROM drive, and the like, and is able to read out computer programs and data recorded on a portable recording medium 404. The application program 404a according to the present embodiment is stored in the portable recording medium 404, where the computer 401 reads out the application program 404a from the portable recording medium 404, and installs the application program 404a to the hard disc 401d.

The application program 404a is not only provided by the portable recording medium 404, but also provided through communication line (wired or wireless) from external devices communicatably connected with the computer 401 through the communication line. For instance, the application program 404a may be stored in the hard disc of the server computer on the internet, so that the computer 401 can access the server computer to download the application program 404a and install the application program 404a to the hard disc 401d.

Operating system providing graphical user interface environment such as Windows (registered trademark) manufactured and sold by U.S. Microsoft Corporation is installed in the hard disc 401d. In the following description, the application program 404a according to the present embodiment is assumed to be operating on the operating system.

The input/output interface 401f is configured by serial interface such as USB, IEEE1394, RS-232C; parallel interface such as SCSI, IDE, IEEE1284; analog interface such as D/A converter, A/D converter, and the like. The keyboard 4c is connected to the input/output interface 401f, so that the user can input data to the computer 401 using the keyboard 4c.

The communication interface 401g is, for example, Ethernet (registered trademark) interface. The computer 401 transmits and receives data with the measurement mechanism unit 2 using a predetermined communication protocol by means of the communication interface 401g.

The image output interface 401h is connected to the display device 4b configured by LCD, CRT, or the like, and is configured to output an image signal corresponding to the image data provided from the CPU 401a to the display device 4b. The display device 4b displays the image (screen) according to the input image signal.

Figure 7:
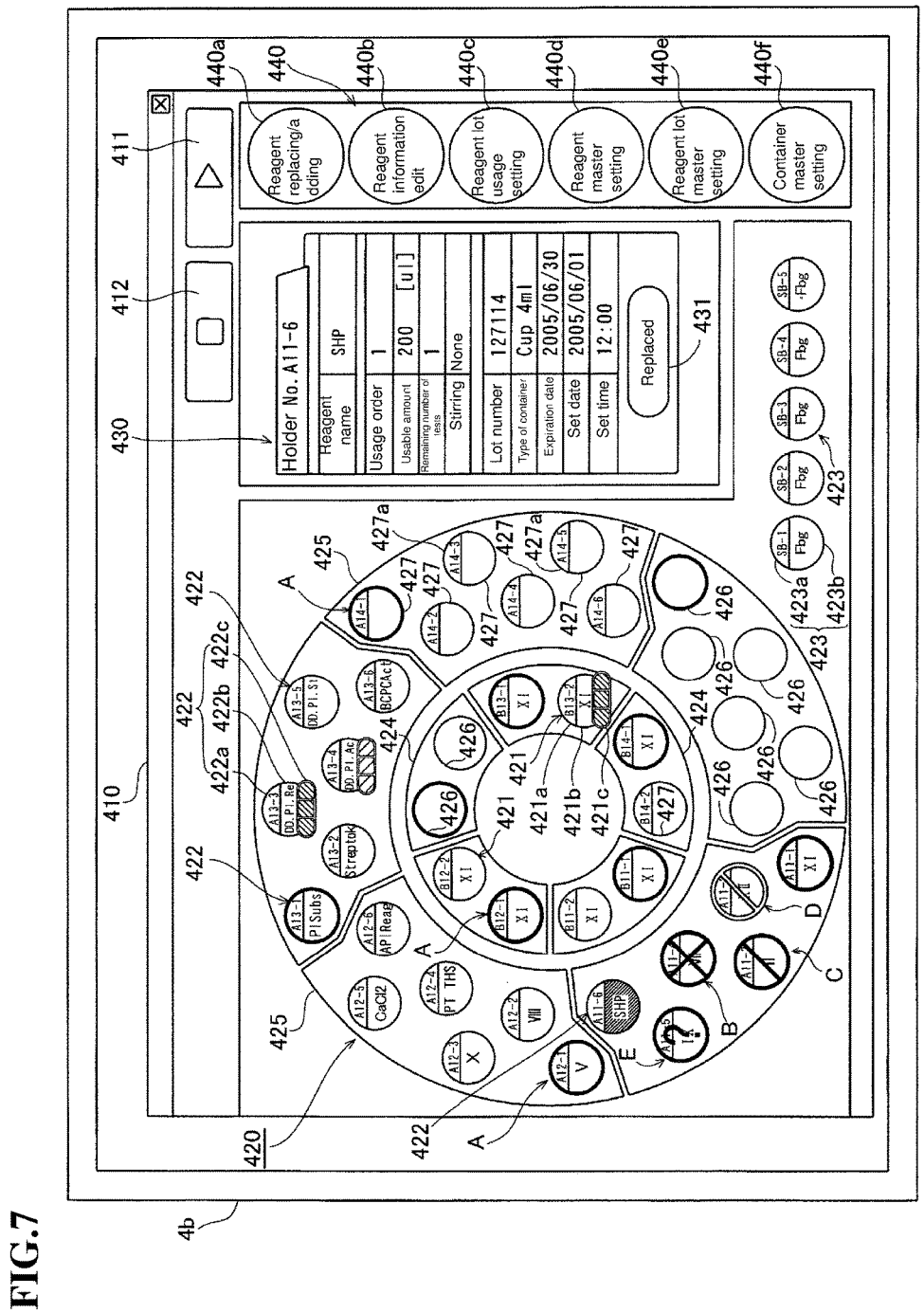
FIG. 7 is a view showing a reagent managing screen displayed on a display device of a control device according to one embodiment of the present invention.

As shown in FIG. 7, in the present embodiment, the display device 4b displays a reagent managing screen 410 that displays the arrangement of the reagents of a reagent storing section 6 to be hereinafter described. The reagent managing screen 410 includes a reagent arrangement displaying region 420, a reagent detailed information displaying region 430, and an operation means displaying region 440. A measurement start button 411 for starting the measurement of the sample analyzer 1 and a measurement stop button 412 for stopping the measurement are arranged on the reagent managing screen 410. The display device 4b has a touch panel function, so that the user can select or operate by directly touching the button etc. displayed on the reagent managing screen 410.

On the reagent arrangement displaying region 420, a maximum of ten first reagent marks 421 displayed in correspondence to the arrangement state of the reagent in a first reagent table 11 on the inner side, to be hereinafter described, a maximum of thirty second reagent marks 422 displayed in correspondence to the arrangement state of the reagent in a second reagent table 12 on the outer side, to be hereinafter described, and a maximum of five diluting/cleaning fluid marks 423 displayed in correspondence to the arranging state of the diluting fluid or the cleaning fluid are displayed in a specifiable manner. The first reagent mark 421 includes a position displaying part 421a for displaying the position of the reagent, a reagent name displaying part 421b for displaying the reagent name, and a remaining amount indicator 421c for displaying the remaining amount of the reagent. Furthermore, the second reagent mark 422 includes a position displaying part 422a for displaying the position of the reagent, a reagent name displaying part 422b for displaying the reagent name, and a remaining amount indicator 422c for displaying the remaining amount of the reagent. The remaining amount indicators 421c and 422c are displayed only when the remaining amount of the reagent becomes less than or equal to a predetermined amount. The diluting/cleaning fluid mark 423 includes a position displaying part 423a for displaying the position of the diluting fluid/cleaning fluid, a fluid name displaying part 423b for displaying a fluid name of the diluting fluid/cleaning fluid, and a remaining amount indicator (not shown) for displaying the remaining amount of the diluting fluid/cleaning fluid.

In the present embodiment, the specified first reagent mark 421, the second reagent mark 422, or the diluting/cleaning fluid mark 423 is displayed so as to be distinguishable from the reagent marks or the diluting/cleaning fluid marks other than the specified reagent marks (first reagent mark 421, second reagent mark 422, or diluting/cleaning fluid mark 423). As shown in FIG. 7, for example, the background with respect to the reagent name of the reagent name displaying part of the non-specified reagent mark is displayed in white (illustrated without hatching (diagonal lines)), whereas the background with respect to the reagent name (e.g., SHP of second reagent mark 422) of the reagent name displaying part of the specified reagent mark is displayed in blue (illustrated with hatching (diagonal lines)).

The positional information (holder number) of the reagent displayed on the position displaying parts 421a and 422a of the first reagent mark 421 and the second reagent mark 422 is displayed by reading barcodes 311b, 312b (see FIG. 15) of a first reagent container rack 310 and barcodes 321b to 326b (see FIG. 16) of a second reagent container rack 320, to be hereinafter described, with a barcode reader 350. The reagent name displayed on the reagent name displaying parts 421b and 422b is displayed with reference to a reagent master (table), to be hereinafter described, based on the values obtained by reading a barcode 300a of a reagent container 300 accommodating the reagent with the barcode reader 350 (see FIG. 5). The position displaying part 423a of the diluting/cleaning fluid mark is always displayed since a holding part 141 (see FIG. 5) of an urgent specimen setting section 140 for holding a diluting/cleaning fluid container (not shown) accommodating the diluting fluid or the cleaning fluid is fixed to the sample analyzer 1. The fluid name displaying part 423b is displayed with reference to the reagent master (table), to be hereinafter described, based on the value obtained by reading a barcode (not shown) of the diluting/cleaning fluid container (not shown) accommodating the diluting fluid or the cleaning fluid with a barcode reader 351.

In the present embodiment, the remaining amount of the reagent displayed on the remaining amount indicators 421c and 422c is calculated by the shape of the reagent container 300 specified with reference to a container master (table) based on the value obtained by reading the barcode 300a of the reagent container 300 with the barcode reader 350, and the height of the fluid level of the reagent accommodated in the reagent container 300. If the calculated remaining amount of the reagent is less than or equal to the predetermined amount, the remaining amount of the reagent is color-coded in correspondence to the remaining amount on the remaining amount indicators 421c and 422c, and a warning is displayed. For instance, if the remaining amount of the reagent is less than or equal to the warning remaining amount, a predetermined color (e.g., yellow (illustrated with left diagonal hatching in "A13-4" of FIG. 7) is displayed on the remaining amount indicators 421c and 422c. If the remaining amount of the reagent is less than or equal to a measurement canceling remaining amount that is less than the warning remaining amount, a predetermined color (e.g., red (illustrated with right diagonal hatching in "A13-3") is displayed on the remaining amount indicators 421c and 422c. If the remaining amount of the reagent is greater than the warning remaining amount, the remaining amount indicators 421c and 422c are not displayed. Since the remaining amount of the reagent is not known for the reagents that have not been used even once since arranged in the reagent table, a predetermined color (e.g., gray (illustrated as region without hatching in "B11-2" of FIG. 19) is displayed on the remaining amount indicator of the reagent mark corresponding to the relevant reagent. The display of remaining amount in such remaining amount indicators 421c and 422c will be hereinafter described in detail.

The remaining amount of the diluting fluid or the cleaning fluid displayed in the remaining amount indicator (not shown) of the diluting/cleaning fluid mark 423 is calculated by the shape of the diluting/cleaning fluid container (not shown) specified with reference to the container master (table) based on the value obtained by reading a barcode (not shown) of the diluting/cleaning container accommodating the diluting fluid or the cleaning fluid with the barcode reader 351 and the height of the fluid level of the diluting fluid or the cleaning fluid accommodated in the diluting/cleaning fluid container.

The first reagent mark 421 is divided into by twos for every first rack mark 424 corresponding to five first reagent container racks 310 (see FIG. 5) capable of holding two reagent containers 300 arranged in the first reagent table 11 (see FIG. 5) and displayed. The second reagent mark 422 is divided into by sixes for every second rack mark 425 corresponding to five second reagent container racks 320 (see FIG. 5) capable of holding six reagent containers 300 arranged in the second reagent table 12 (see FIG. 5) and displayed. That is, the reagent managing screen 410 allows checking of at which position of which reagent container rack (first reagent container rack 310 or second reagent container rack 320) of which reagent table (first reagent table 11 or second reagent table 12) the reagent is arranged.

If the reagent container rack is not arranged on the reagent table, a circular rack non-arranged mark 426 with nothing shown on the inside is displayed at a region corresponding to the portion the reagent container rack is not arranged. If the first reagent container rack 310 or the second reagent container rack 320 is arranged on the first reagent table 11 or the second reagent table 12, and the reagent container 300 to be held by the reagent container rack is not present, a reagent non-arranged mark 427 is displayed at a region corresponding to the portion the reagent is not arranged. The reagent non-arranged mark 427 has a position displaying part 427a for displaying positional information (holder number) of the portion the reagent is not arranged. This aspect will be hereinafter described in detail.

Among the first reagent mark 421, the second reagent mark 422, the rack non-arranged mark 426, and the reagent non-arranged mark 427, the mark positioned at a predetermined position has the outer periphery of the mark shown in a predetermined color (e.g., brown (illustrated with heavy line). The mark A which outer periphery is shown in brown indicates that the reagent arranged at the relevant position is to be stirred. The reagent that needs stirring is arranged at the position of the mark A which outer periphery is shown in brown.

In the present embodiment, if the reagent that needs to be stirred is not arranged at the position of the mark A which outer periphery is shown in brown, a mistaken arrangement mark B (e.g., red x mark) is displayed on the reagent mark of the reagent that needs stirring. An expired mark C (e.g., one red diagonal line (illustrated with heavy line in the figure)) is displayed for the reagent mark of the reagent which has expired, as hereinafter described. The sample analyzer 1 is configured so as not to use the reagent corresponding to the reagent mark shown with the reagent mistaken arrangement mark or expired mark for measurement. A stable time-out mark D (e.g. one yellow diagonal line (illustrated with outlined line in the figure) is displayed for the reagent mark of the reagent that has elapsed a predetermined time (e.g., eight hours) from a set date or set time of the reagent, as hereinafter described. When reading of the barcode 300a of the reagent container 300 by the barcode reader 350 fails, a barcode reading error mark E (e.g., "?" mark) is displayed on the reagent mark of the reagent accommodated in the reagent container which reading has failed.

On the reagent detailed information displaying region 430, detailed information (holder number, reagent name, usage order, usable remaining amount (usable amount), remaining number of tests, necessity of stirring, lot number, type of reagent container, expiration date of reagent, set date, set time etc.) of the reagent corresponding to the specified first reagent mark 421 or the second reagent mark 422 are displayed. More specifically, positional information of the reagent displayed at a position displaying part of the specified reagent mark is displayed on the "holder number" column. Similar to the reagent name displaying part of the specified reagent mark, the reagent name specified with reference to the reagent master based on the value obtained by reading the barcode 300a of the reagent container 300 with the barcode reader 350 is displayed on the "reagent name" column. The order of use in the measurement when a plurality of the same reagents is arranged on the reagent table is displayed on the "usage order" column. The remaining amount of the reagent corresponding to the specified reagent mark is displayed on the "usable amount" column. The value obtained by dividing the "usable amount" by the reagent amount to be used in one measurement is displayed on the "remaining number of tests". Whether or not the reagent corresponding to the specified reagent mark needs to be stirred is displayed on the "stirring" column. The lot number specified with reference to the reagent lot master based on the value obtained by reading the barcode 300a of the reagent container 300 with the barcode reader 350 is displayed on the "lot number" column. The type of container specified with reference to the container master based on the value obtained by reading the barcode 300a of the reagent container 300 with the barcode reader 350 is displayed on the "type of container" column. The expiration date corresponding to the lot number specified with reference to the reagent lot master based on the value obtained by reading the barcode 300a of the reagent container 300 with the barcode reader 350 is displayed on the "expiration date" column. The date and time the reagent corresponding to the specified reagent mark was set in the sample analyzer 1 are displayed on the "set date" column and the "set time" column. The user is able to manage the reagents, e.g. to determine the changing timing of the reagent with the detailed information of the reagent. If the reading of the barcode failed and the detailed information of the reagent are not displayed, the detailed information of the reagent can be edited with a reagent information edit button 440b and a reagent information edit dialogue 450, as hereinafter described. The display of the detailed information of the reagent in the reagent detailed information displaying region 430 will be hereinafter described in detail.

A "replaced" button 431 is arranged on the reagent detailed information displaying region 430. The "replaced" button 431 has a function of having the sample analyzer 1 recognize that replacement of the reagent has been performed by hand when the replaced reagent is not recognized by the sample analyzer 1 when the reagent is replaced. The "set date" and the "set time" of the reagent displayed information displaying region 430 are updated to the time the "replaced" button 431 was pushed by pushing the "replaced" button 431.

The operation means displaying region 440 includes a replacement/addition instructing button 440a for instructing replacement and addition of the reagent, the edit button 440b for editing the reagent information, a reagent lot setting button 440c for assigning the reagent lot to the measurement item, a reagent master setting button 440d, a reagent lot master setting button 440e, and a container master setting button 440f.

In the present embodiment, when the replacement/addition instructing button 440a is selected with the first reagent mark 421 or the second reagent mark 422 specified, the first reagent container rack 310 or the second reagent container rack 320 holding the reagent container 300 that accommodates the reagent corresponding to the specified reagent mark is moved to a retrieving position enabling retrieval from the sample analyzer 1. When addition of the reagent is performed, the replacement/addition instructing button 440a is selected with the reagent non-arranged mark 427 specified. The first reagent container rack 310 or the second reagent container rack 320 corresponding to the rack mark including the specified reagent non-arranged mark is thus moved to the retrieving position. Similarly, when the replacement/addition button 440a is selected with the diluting/cleaning fluid mark 423 specified, the diluting fluid or the cleaning fluid can be replaced or added.

Figure 8:
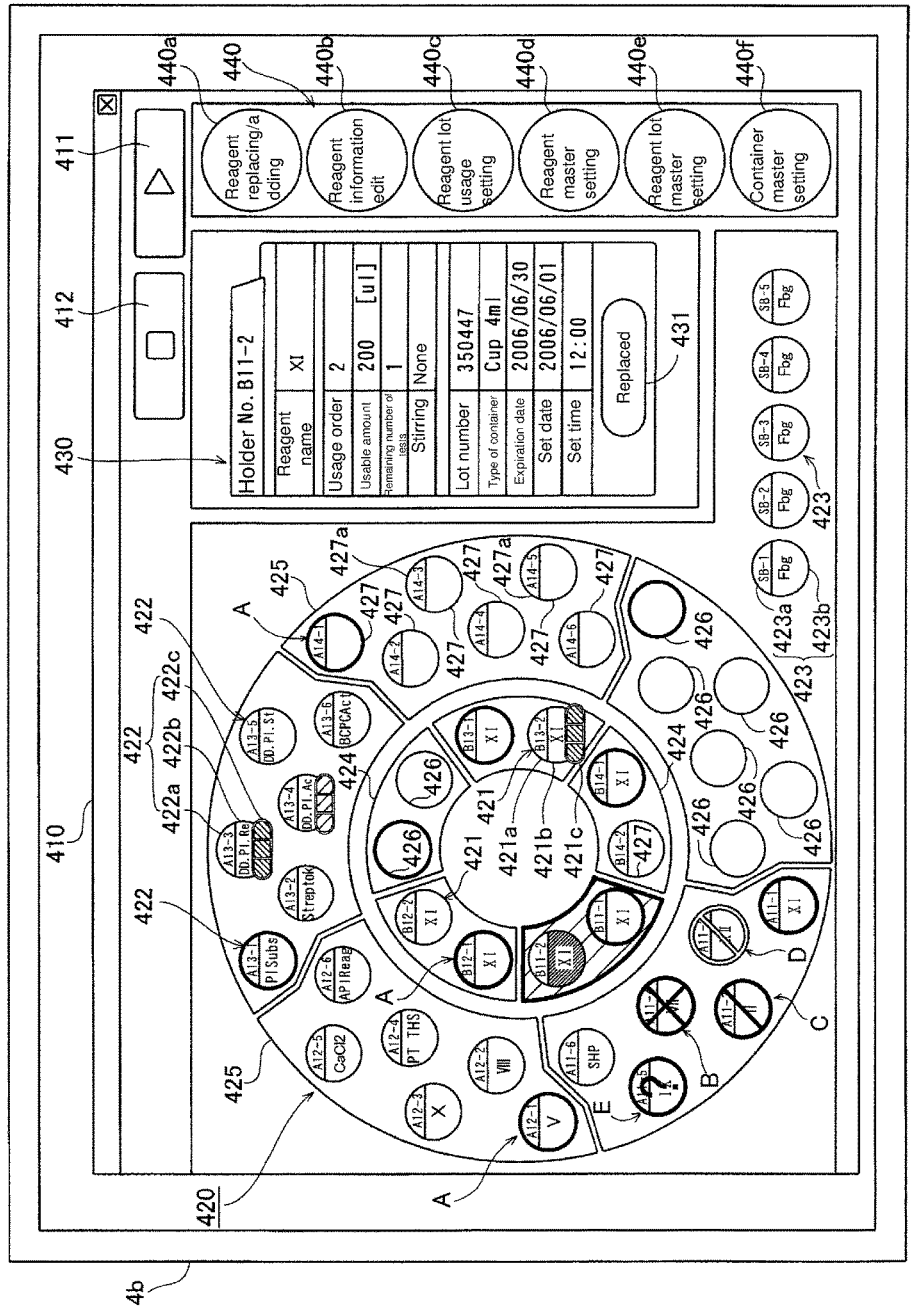
FIG. 8 is a view showing a reagent managing screen displayed on a display device of a control device according to one embodiment of the present invention.
Figure 9:
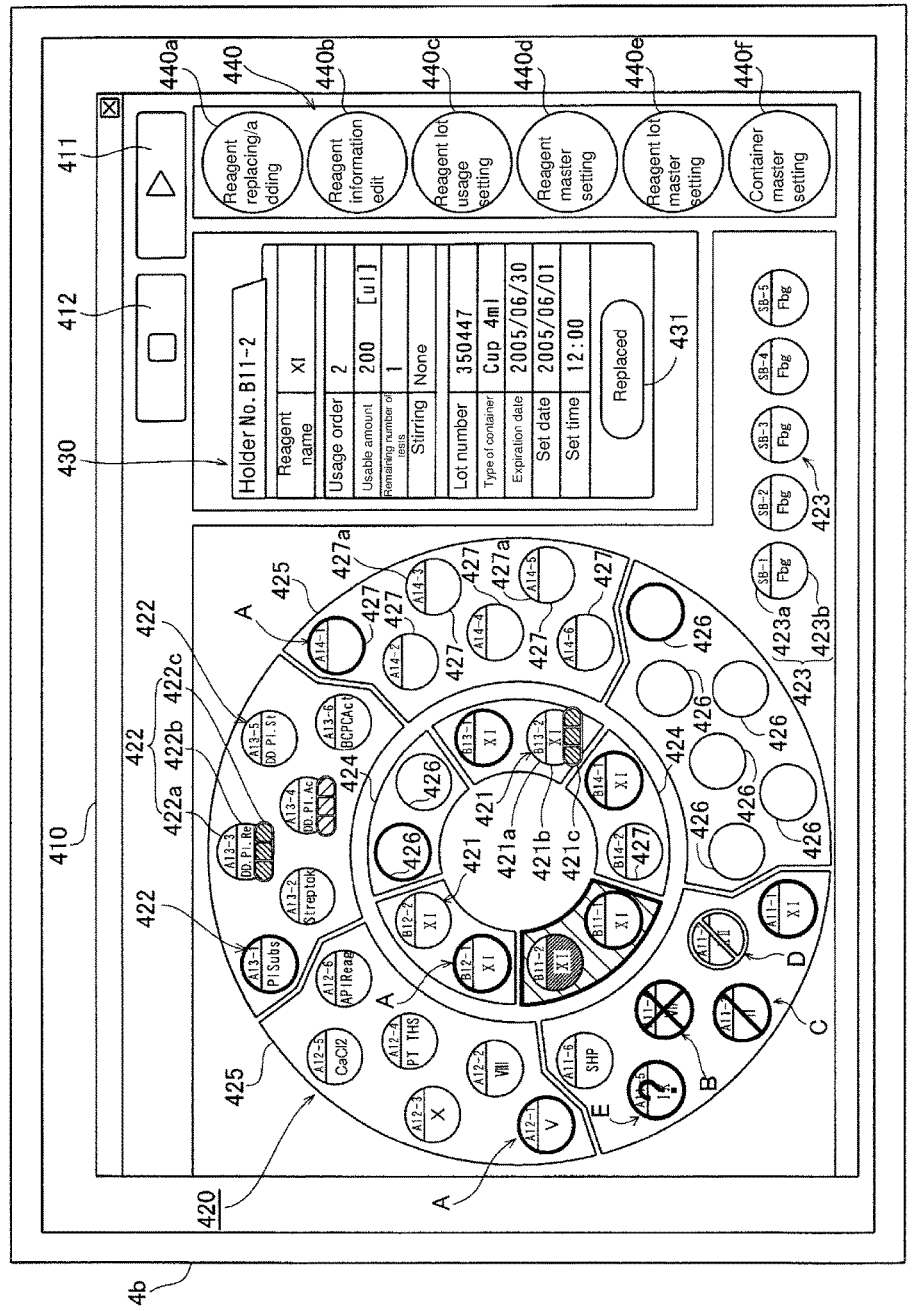
FIG. 9 is a view showing a reagent managing screen displayed on a display device of a control device according to one embodiment of the present invention.
Figure 10:
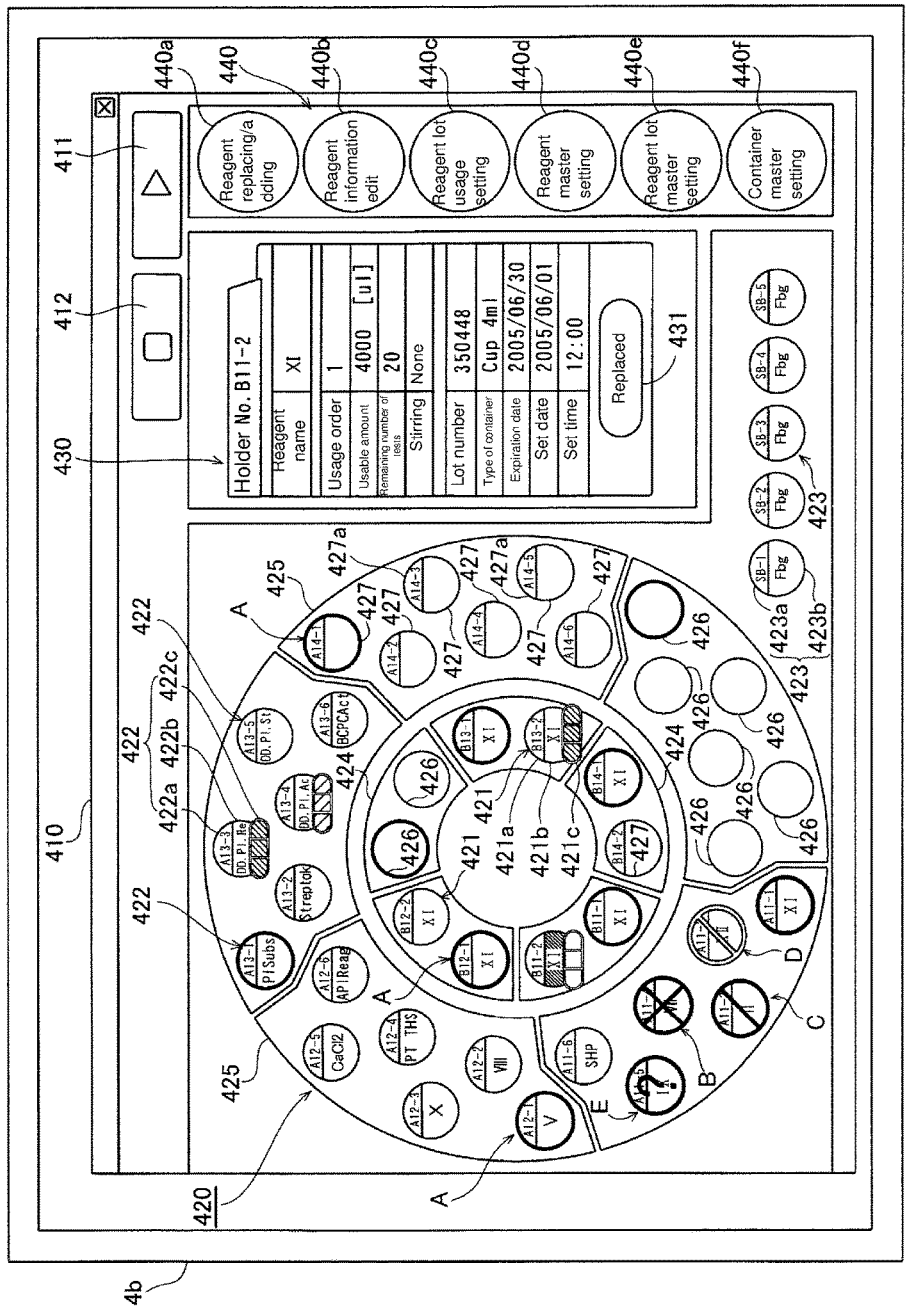
FIG. 10 is a view showing a reagent managing screen displayed on a display device of a control device according to one embodiment of the present invention.

Furthermore, in the present embodiment, a function of color-coding and displaying so as to be identifiable by the user a waiting position from when the replacement/addition button 440a is pushed until the reagent container rack corresponding to the rack mark including specified first reagent mark 421, the second reagent mark 422, or the reagent non-arranged mark 427 is moved to the retrieving position and a retrievable state in which the reagent container rack can be retrieved to the outside from the retrieving position is provided. That is, as shown in FIG. 8, the first rack mark 424 or the second rack mark 425 including the specified first reagent mark 421, the second reagent mark 422, or the reagent non-arranged mark 427 is displayed in a predetermined color (e.g., yellow) in the waiting state. In FIG. 8, the reagent of "B11-2" is the target of replacement, and thus the rack mark including the reagent of "B11-2" is displayed in the predetermined color (e.g., yellow (illustrated in left diagonal hatching in FIG. 8). As shown in FIG. 9, the first rack mark 424 or the second rack mark 425 is displayed in a predetermined color (e.g., green) in the retrievable state. In FIG. 9, the rack mark including the reagent of "B11-2" is displayed in the predetermined color (e.g., green (illustrated in right diagonal hatching in FIG. 9)). The replacement and addition of the reagent will be hereinafter described in detail.

Figure 11:
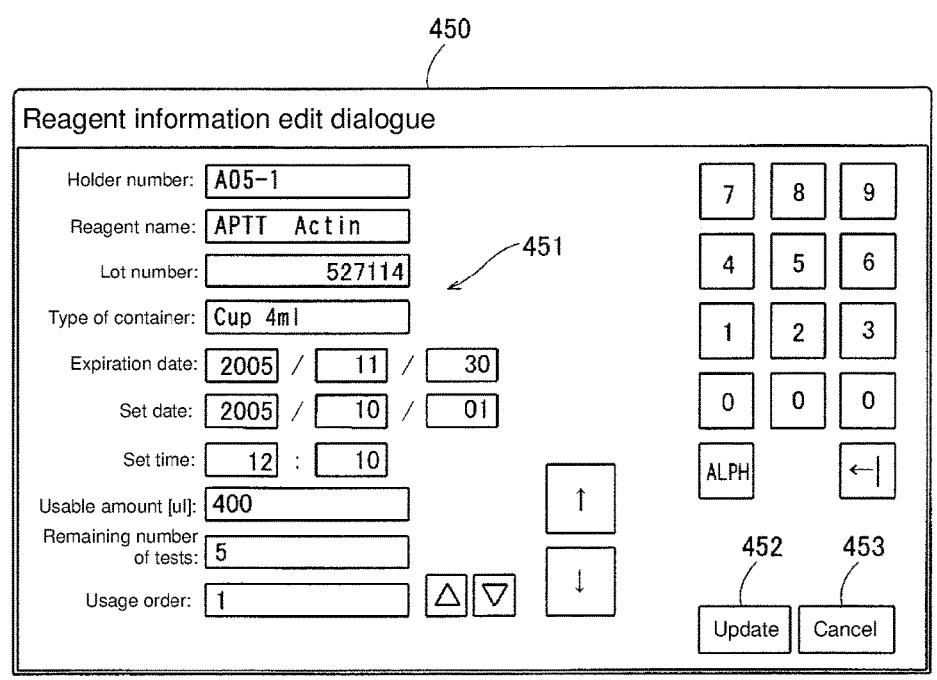
FIG. 11 is a view showing a reagent information edit dialogue displayed on the display device of the control device according to one embodiment of the present invention.

Moreover, in the present embodiment, the detailed information of the reagent corresponding to the specified reagent mark can be edited by pushing the reagent information edit button 440b in the reagent mark specified state. Specifically, the reagent information edit dialogue 450 is displayed when the reagent edit button 440b is pushed, as shown in FIG. 11. The reagent information edit dialogue 450 includes a setting changing work region 451 for changing each item ("lot number", "set date", "expiration date", etc.) of the detailed information, an update button 452, and a cancel button 453. After the user edits the detailed information in the setting changing work region 451, the edited detailed information is reflected on the reagent detailed information displaying region 430 by pushing the update button 452. The editing of the detailed information is canceled by pushing the cancel button 453. The editing of the detailed information of the reagent will be hereinafter described in detail.

Figure 12:
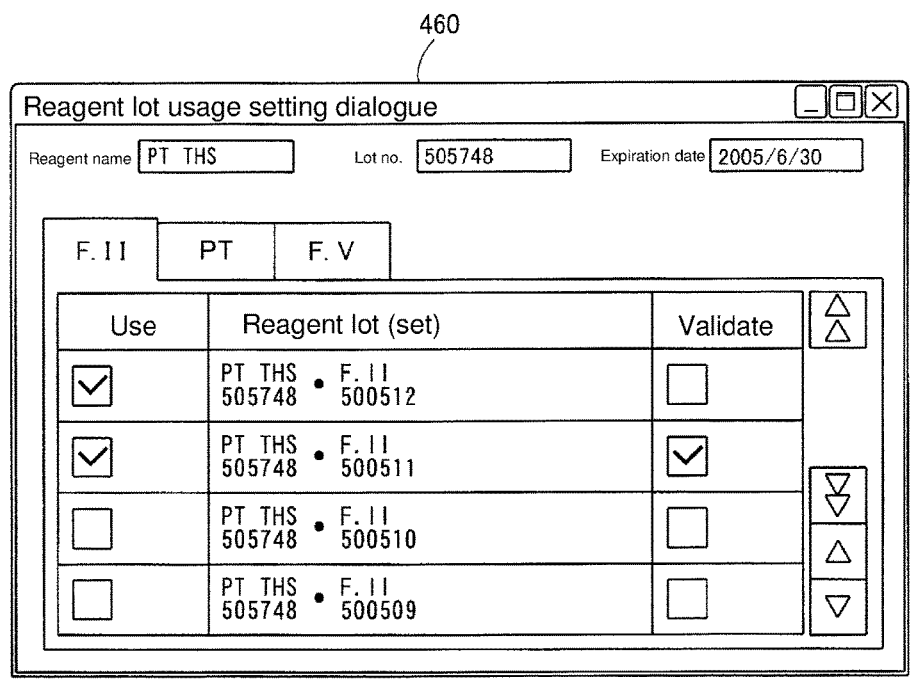
FIG. 12 is a view showing a reagent lot usage setting dialogue displayed on the display device of the control device according to one embodiment of the present invention.

The reagent lot usage setting button 440c has a function of displaying a reagent lot usage setting dialogue 460 for setting whether the respective lot or the combination of the lots are usable with respect to the plurality of reagent lots or the combination of the plurality of reagent lots for each measurement item. The specific example will be described with reference to FIG. 12. In FIG. 12, a case where "PT THS" and "F.II" is used as the reagent used in the measurement item "F.II" is shown. Four lot numbers "500509" to "500512" are usable in reagent "F.II", and one lot number "505748" is usable in reagent "PT THS". That is, in FIG. 11, four types of combination are obtained for the combination of reagent "PT THS" and reagent "F.II" when measuring the measurement item "F.II". The user can set which combination out of the four types of combinations to use for the measurement in the reagent lot usage setting dialogue 460. The checkbox "use" has a function of setting whether to use the combination of the corresponding reagents for precision managing measurement and calibration curve measurement. The checkbox "validate" has a function of setting whether to use the combination of the corresponding reagents for the normal specimen measurement. That is, in the example of FIG. 11, the combination of the reagent "PT THS" (lot number 505748) and the reagent "F.II" (lot number 500512) is set so as to be used for the precision managing measurement and the calibration curve measurement, but not to be used for the normal specimen measurement. The combination of the reagent "PT THS" (lot number 505748) and the reagent "F.II" (lot number 500511) is set so as to be used for the precision managing measurement and the calibration curve measurement, and to be also used for the normal specimen measurement. The combination of the reagent "PT THS" (lot number 505748) and the reagent "F.II" (lot number 500510 or 500509) is set so as not to be used for the precision managing measurement and the calibration curve measurement, and also not to be used for the normal specimen measurement. The plurality of reagents having different lot numbers in one type of reagent thus can be assigned for each measurement item.

The reagent master setting button 440d has a function of displaying a reagent master setting dialogue (not shown) for setting the reagent master (table) having a correspondence relationship between the value read from the barcode 300a of the reagent container 300 and the reagent name. The reagent lot master setting button 440e has a function of displaying a reagent lot master setting dialogue (not shown) for setting the reagent lot master (table) having a correspondence relationship between the value read from the barcode 300a of the reagent container 300 and the reagent lot and expiration date. The container master setting button 440f has a function of displaying a container master setting dialogue (not shown) for setting the container mater (table) having a correspondence relationship between the value read from the barcode 300a of the reagent container 300 and the type of the reagent container 300.

Figure 3:
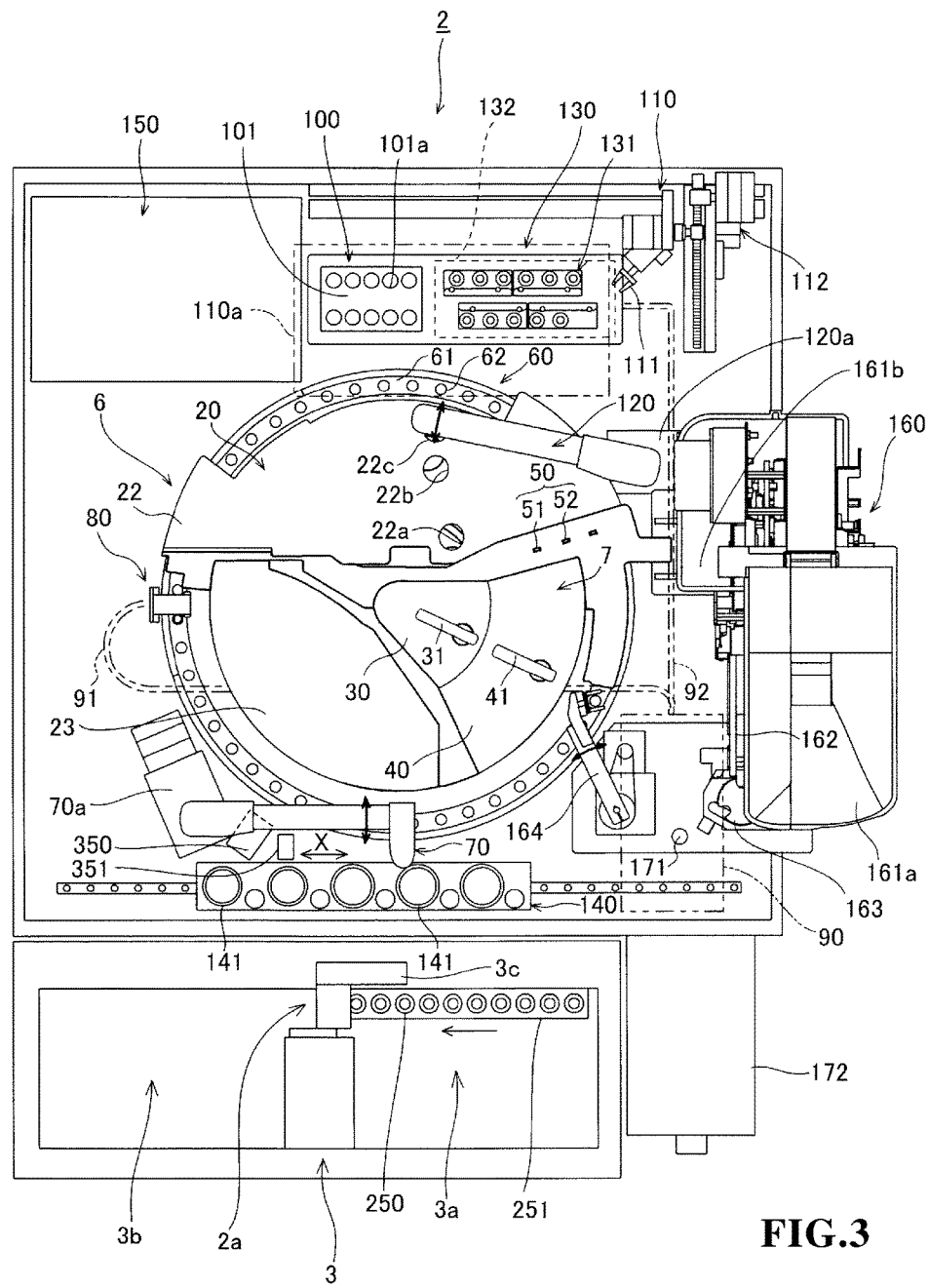
FIG. 3 is a plan view showing a measurement mechanism unit of the sample analyzer according to one embodiment of the present invention.

As shown in FIGS. 1 to 3, the specimen conveyance mechanism unit 3 is adapted to convey a rack 251 mounted with a plurality of (ten in the present embodiment) test tubes 250 accommodating the specimen to a suction position 2a (see FIG. 3) of the measurement mechanism unit 2 to supply the specimen to the measurement mechanism unit 2. The conveyance mechanism unit 3 includes a rack set region 3a for setting the rack 251 in which the test tubes 250 accommodating non-processed blood specimen are accommodated, and a rack accommodating region 3b for accommodating the rack 251 in which the test tubes 250 accommodating processed specimen are accommodated.

The measurement mechanism unit 2 is configured to perform optical measurement on the specimen supplied from the conveyance mechanism unit 3 to acquire optical information related to the supplied specimen. In the present embodiment, optical measurement is performed on the specimen dispensed into a cuvette 200 of the measurement mechanism unit 2 from the test tube 250 mounted on the rack 251 of the conveyance mechanism unit 3. The measurement mechanism unit 2 includes a reagent storing section 6 for storing the reagents and a reagent replacing section 7 for replacing or adding the reagent, as shown in FIG. 3.

As shown in FIG. 17, the measurement mechanism unit 2 includes a specimen dispensing driving section 70a, a reagent dispensing driving section 120a, a first driving section 502, a second driving section 503, a first lock detecting section 504, a second lock detecting section 505, the reagent barcode reader 350, the specimen barcode reader 3c, a first optical information acquiring section 80, a second optical information acquiring section 130, and a control section 501 electrically connected to the conveyance mechanism unit 3 and the like.

The measurement dispensing driving section 70a includes a stepping motor part 70b having a function of rotating and moving up and down the specimen dispensing arm 70 (see FIGS. 3 and 5), to be hereinafter described, a drive circuit (not shown) for driving the stepping motor portion 70b, and a pump (not shown) for pumping and dispensing the specimen.

The reagent dispensing driving section 120a includes a stepping motor part 120b having a function of rotating and moving up and down the reagent dispensing arm 120 (see FIGS. 3 and 5), to be hereinafter described, a drive circuit (not shown) for driving the stepping motor 120b, and a pump (not shown) for pumping and dispensing the reagent.

The first driving section 502 includes a first stepping motor (not shown) having a function of rotating the first reagent table 11 (see FIG. 5), to be hereinafter described, and a drive circuit (not shown) for driving the first stepping motor. The first reagent table 11 rotates by the amount corresponding to the number of pulses of the driving pulse signal provided from the control section 501 to the first driving section 502, and then stops.

Similarly, the second driving section 503 includes a second stepping motor (not shown) having a function of rotating the first reagent table 12 (see FIG. 5), to be hereinafter described, and a drive circuit (not shown) for driving the second stepping motor. The second reagent table 12 rotates by the amount corresponding to the number of pulses of the driving pulse signal provided from the control section 501 to the second driving section 503, and then stops.

The control section 501 counts the number of pulses of the provided driving pulse signal to determine the amount of rotation movement of each reagent table 11, 12 from the position of origin of the first reagent 11 and the second reagent table 12, and controls the rotation movement of each reagent table 11, 12.

The first lock detecting section 504 has a function of detecting a locked state of a first lid 30 (see FIG. 3), to be hereinafter described, and transmitting a lock signal to the control section 501 when locked.

Similarly, the second lock detecting section 505 has a function of detecting a locked state of a second lid 40 (see FIG. 3), to be hereinafter described, and transmitting a lock signal to the control section 501 when locked.

The reagent barcode reader 350 has a function of reading each barcode on the first reagent table 11 and the second reagent table 12, and is arranged in the vicinity of the side surface 21 of the reagent storing section 6, to be hereinafter described, with a predetermined distance from the reagent storing section 6 (see FIGS. 3 to 5). The reagent barcode reader 350 is able to transmit and receive data with the control section 501, and also includes a drive circuit (not shown) for ON/OFF controlling the reagent barcode reader 350. The position of the reagent barcode reader 350 is always fixed.

Figure 4:
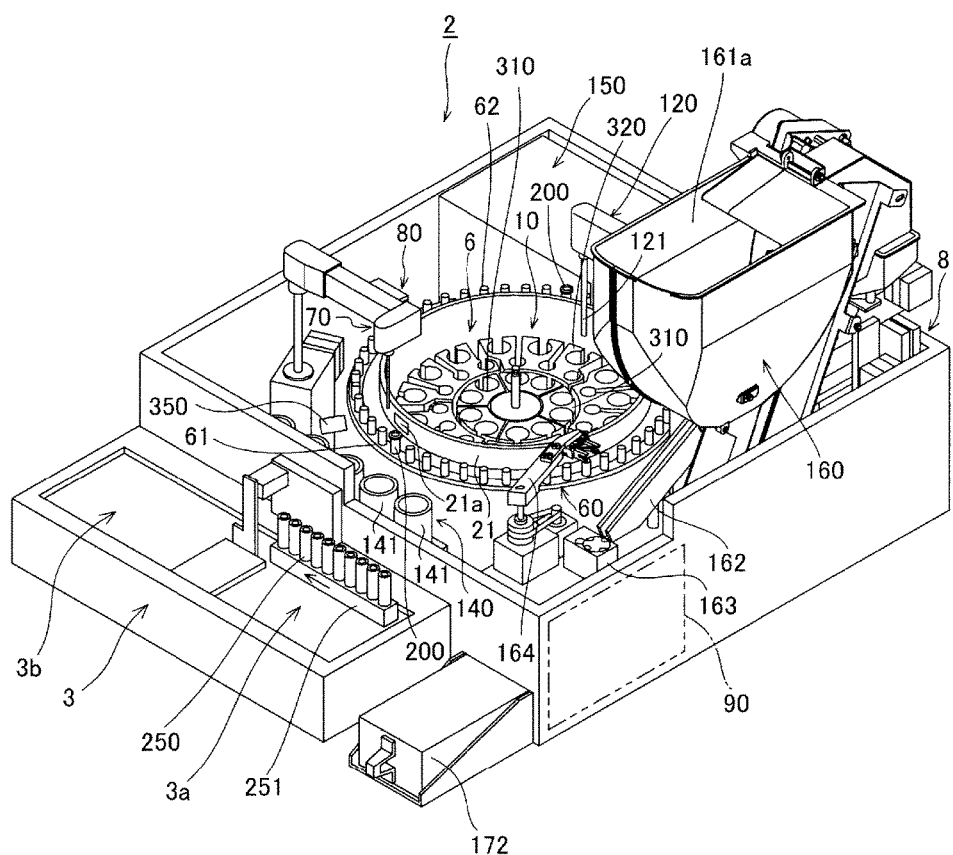
FIG. 4 is a perspective view showing the interior of the measurement mechanism unit and a reagent storing section of the sample analyzer according to one embodiment of the present invention.
Figure 5:
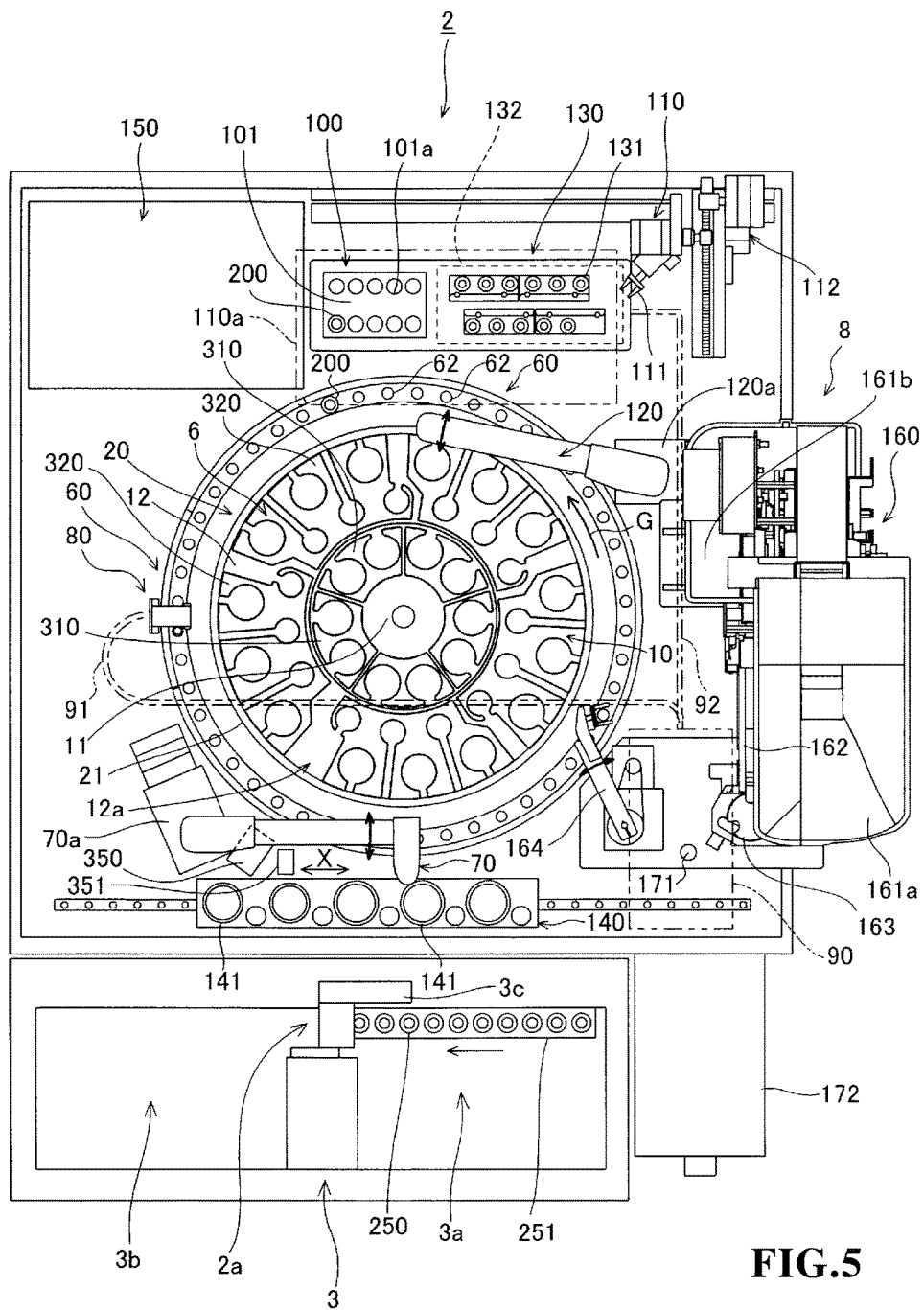
FIG. 5 is a plan view showing the interior of the measurement mechanism unit and the reagent storing section shown in FIG. 4.
Figure 6:
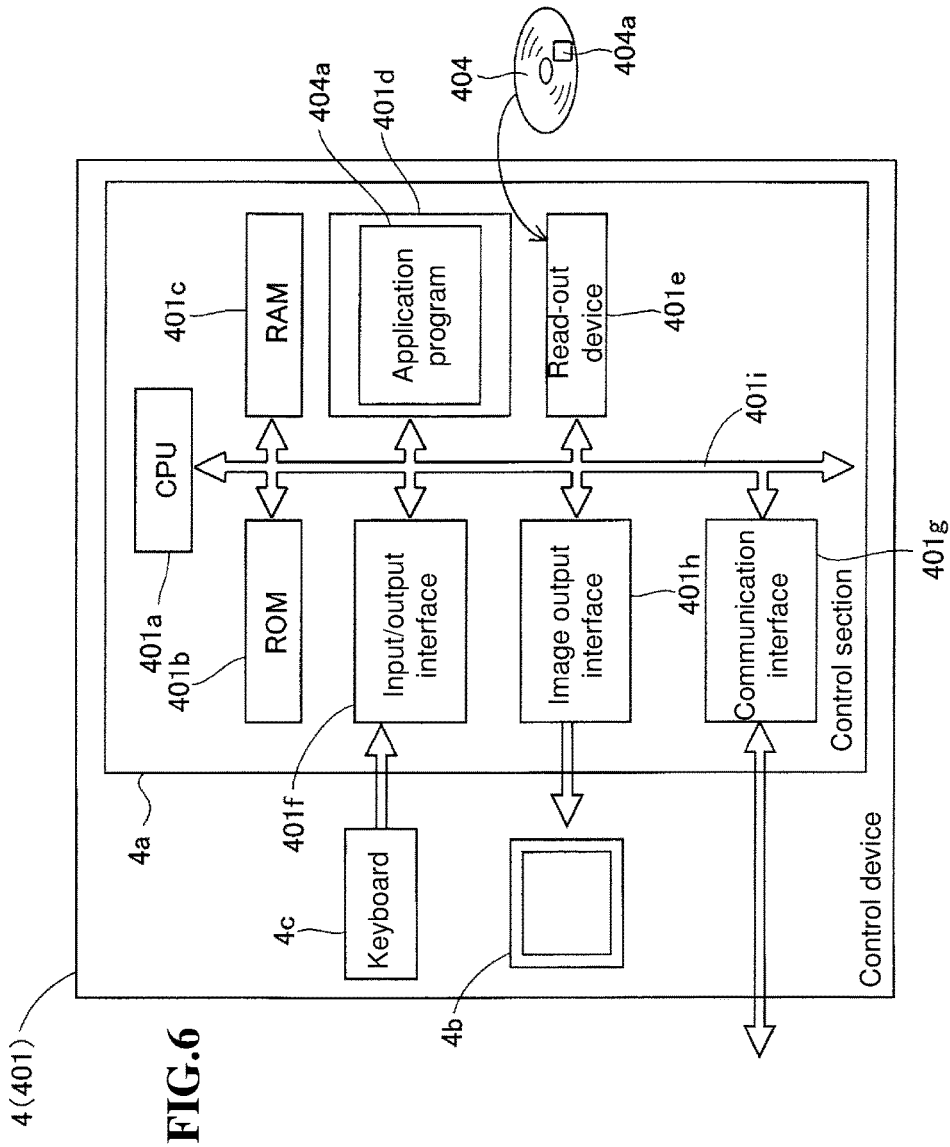
FIG. 6 is a block diagram showing a control device of the sample analyzer according to one embodiment of the present invention.

The specimen barcode reader 3c has a function of reading the barcode attached to the test tube 250 in which the specimen mounted on the rack 251 conveyed by the conveyance mechanism unit 3 is accommodated, and is arranged in the vicinity of the suction position 2a of the measurement mechanism unit 2 described above so as to face the rack 251 conveyed by the conveyance mechanism unit 3 (see FIGS. 3 to 5). The specimen barcode reader 3c is able to transmit and receive data with the control section 501, and also includes a drive circuit (not shown) for ON/OFF controlling the specimen barcode reader 3c. The position of the specimen barcode reader 3c is always fixed.

The first optical information acquiring section 80 and the second optical information acquiring section 130 (see FIGS. 3 and 5) respectively has a function of acquiring the optical information of the specimen, and is configured to transmit and receive data with the control section 501. The details of the first optical information acquiring section 80 and the second optical information acquiring section 130 will be hereinafter described in detail.

As shown in FIG. 18, the control section 501 is mainly configured by a CPU 501a, a ROM 501b, a RAM 501c, and a communication interface 501d.

The CPU 501a executes computer programs stored in the ROM 501b and the computer programs loaded in the RAM 501c. The ROM 501b is recorded with computer programs to be executed by the CPU 501a, data used for executing the computer program, and the like. The RAM 501c is used to read out the computer programs recorded on the ROM 501b. The RAM 501c is used as a work region of the CPU 501a when executing the computer programs.

The communication interface 501d is connected to the control device 4, and has a function of transmitting optical information of the specimen to the control device 4 and receiving the signal form the control section 4a of the control device 4. The communication interface 501d has a function of transmitting commands from the CPU 501a to drive each section of the conveyance mechanism unit 3 and the measurement mechanism unit 2.

As shown in FIG. 3, the measurement mechanism unit 2 includes the reagent storing section 6 for storing the reagent and the reagent replacing section 7 for replacing or adding the reagent.

The reagent storing section 6 is arranged to refrigerate the reagent container 300 accommodating the reagent to be applied to the specimen in the cuvette 200 at low temperature (about 10° C.) and to convey the reagent container 300 in the rotating direction. The alteration of the reagent is suppressed by storing the reagent at low temperature. The reagent storing section 6 includes a reagent conveying part 10 (see FIGS. 4 and 5) for holding and rotation conveying the reagent and an outer wall part 20 (see FIG. 3) arranged so as to cover the periphery and the upper side of the reagent conveying part 10, as shown in FIGS. 3 to 5. The reagent conveying part 10 holding the reagent is arranged in the refrigerating region formed by the outer wall part 20, and a first lid 30 and a second lid 40 of the reagent replacing section 7, to be hereinafter described.

As shown in FIG. 5, the reagent conveying part 10 includes the first reagent table 11 of circular shape, and the second reagent table 12 of circular ring shape arranged concentrically with respect to the first reagent table 11 on the outer side of the first reagent table 11 of circular shape. The first reagent table 11 and the second reagent table 12 are respectively configured so that the first reagent container rack 310 and the second reagent container rack 320 for holding the reagent container 300 can be removably arranged. The outer wall part 20 is configured by a side face 21 (see FIG. 4), an upper face 22 (see FIG. 3) fixed to the side face 21, and a detachable lid 23 (see FIG. 3). The barcode reader 350 is arranged in the vicinity of the side face 21 (see FIG. 4) of the reagent storing section 6 at a predetermined distance with the reagent storing section 6.

The first reagent table 11 and the second reagent table 12 are respectively configured so as to be rotatable both in the clockwise direction and in the counterclockwise direction, where each table is rotatable independent from each other. The first reagent container rack 310 and the second reagent container rack 320 for holding the reagent container 300 accommodating the reagent are respectively conveyed in the rotating direction by the first reagent table 11 and the second reagent table 12. The reagent to be dispensed can be arranged close to the reagent dispensing arm 120 when the reagent dispensing arm 120, to be hereinafter described, dispenses the reagent by conveying the reagent container 300 in the rotating direction.

Furthermore, a heat insulation material (not shown) is attached to the side face 21 of the outer wall part 20 so that cooled air in the reagent storing section 6 (refrigerating region) does not escape. As shown in FIG. 4, a shutter 21a that can be opened and closed is arranged at a position facing the barcode reader 350 of the side face 21 of the outer wall part 20. The shutter 21a is configured to open only when reading the barcode of the reagent container 300, the first reagent container rack 310, and the second reagent container rack 320 by the barcode reader 350. The cooled air in the reagent storing section 6 (refrigerating region) is thereby suppressed from escaping outside.

As shown in FIG. 3, the upper face 22 of the outer wall part 20 includes three holes 22a, 22b, and 22c. The suction of the reagent stored in the reagent storing section 6 is performed by the reagent dispensing arm 120 through the three holes 22a, 22b, and 22c. The hole 22a is positioned above the reagent container 300 held at the first reagent container rack 310. The suction of the reagent is performed from the reagent container 300 held at the first reagent container rack 310 through the hole 22a. The holes 22b and 22c are positioned above the reagent container 300 held in the back row and the front row of the second reagent container rack 320. The suction of the reagent is performed from the reagent container 300 held at the back row and the front row of the second reagent container rack 320 through the holes 22b and 22c.

A semicircular opening is formed in the reagent storing section 6 (refrigerating region) by detaching the lid 23 with the first lid 30 and the second lid 40, to be hereinafter described. When starting the measurement in the sample analyzer 1, the first reagent container rack 310 and the second reagent container rack 320 are arranged in the reagent storing section 6 through such opening.

Figure 13:
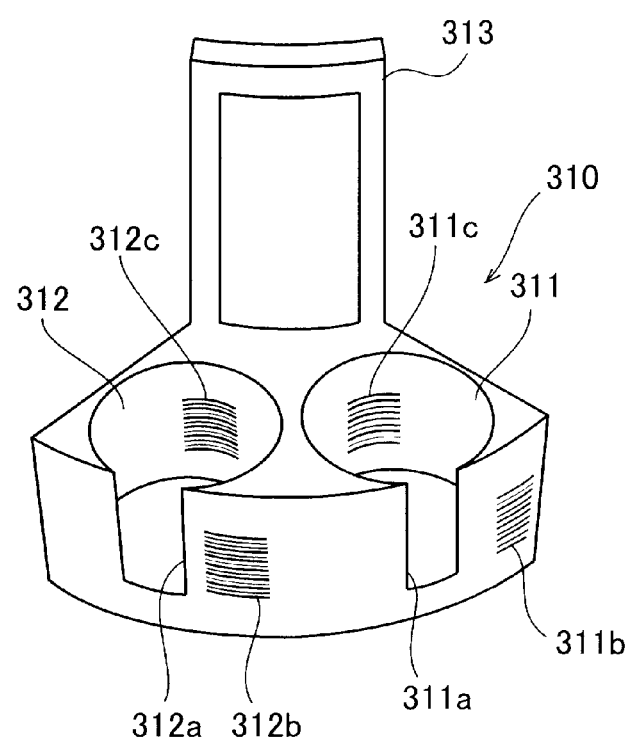
FIG. 13 is a perspective view showing a first reagent container rack according to one embodiment.

As shown in FIG. 5, five first reagent container racks 310 can be arranged in the first reagent table 11. The reagent containers 300 are arranged in a circular ring form in these five first reagent container racks 310. As shown in FIGS. 13 and 15, the first reagent container rack 310 includes two holding parts 310 and 312 for holding the reagent container 300, cut-out portions 311a and 312a respectively arranged on the front face side of the holding parts 311 and 312, and one gripping part 313 arranged so as to project upward. Moreover, as shown in FIG. 13, the holding parts 311 and 312 are formed into a circular form in plan view, and are able to hold the reagent container 300 when the reagent container 300 of cylindrical shape is inserted thereto. The reagent container 300 having an outer diameter smaller than the inner diameter of the holding parts 311 or 312 can be held by the holding part 311 or 312 by attaching an adapter (not shown) to the holding part 311 or 312. The first reagent container rack 310 includes two types of racks formed so that the combination of the inner diameters of the holding parts 311 and 312 is different. The user can respond to the reagent container 300 of various sizes by appropriately changing the type of rack. Barcodes 311b and 312b are respectively arranged on the front face side of the outer surface of the holding parts 311 and 312, and barcodes 311c and 312c are respectively arranged on the inner surface of the holding parts 311 and 312.

The two holding parts 311 and 312 can hold a plurality of reagent containers 300 accommodating various reagents to be added when preparing measurement sample from a specimen one by one. That is, a maximum of ten (2×5=10) of reagent containers 300 can be arranged on the first reagent table 11. Each cut-out portion 311a and 312a is arranged to read the barcodes 311c and 312c with the barcode reader 350 (see FIG. 5). The gripping part 313 is gripped when taking out the first reagent container rack 310 from the reagent storing section 6.

Each barcode 311b and 312b includes positional information (holder number) for identifying the position of the holding parts 311 and 312. The barcodes 311c and 312c include information (no reagent container information) indicating that the reagent container 300 held by the holding parts 311 and 312 does not exist. Furthermore, the barcode 300a of the reagent container 300 includes information for specifying the detailed information (information of reagent name, type of reagent container, lot number, expiration date of reagent, etc.) of the reagent accommodated in the reagent container 300.

If the reagent container 300 is held in the holding part 311, for example, the barcode 311c is not read and the barcode 300a of the reagent container 300 is read. That is, if the barcode 300a is read after reading the barcode 311b with the barcode reader 350, the control section 4a recognizes that the reagent having the reagent information from the barcode 300a is held in the holding part 311. In the reagent arrangement displaying region 420 of the reagent managing screen 410, the first reagent mark 421 is displayed at a position corresponding to the holding part 311. When the barcode 311c is read after the barcode 311b is read by the barcode reader 350, the control section 4a recognizes that the reagent container 300 being held at the holding part 311 does not exist. In the reagent arrangement displaying region 420 of the reagent managing screen 410, the reagent non-arranged mark 427 is displayed at the position corresponding to the holding part 311. If either the barcode 300a or the barcode 311c is read after the barcode 311b is read by the barcode reader 350 (when reagent container 300 is facing the side), the control section 4a recognizes a reading error and to display a barcode reading error mark E indicating that reading has failed on the display device 4b. If the first reagent container rack itself is not arranged in the first reagent table 11, the barcode reader 350 is configured so as not to read the barcodes 311b, 312b, 311c, 312c of the first reagent container rack 310 and the barcode 300a of the reagent container 300. Thus, in the reagent arrangement display region 420 of the reagent managing screen 410, the rack non-arranged mark 426 is displayed on the first rack mark 424 corresponding to the portion not arranged with the first reagent container rack 310.

Figure 14:
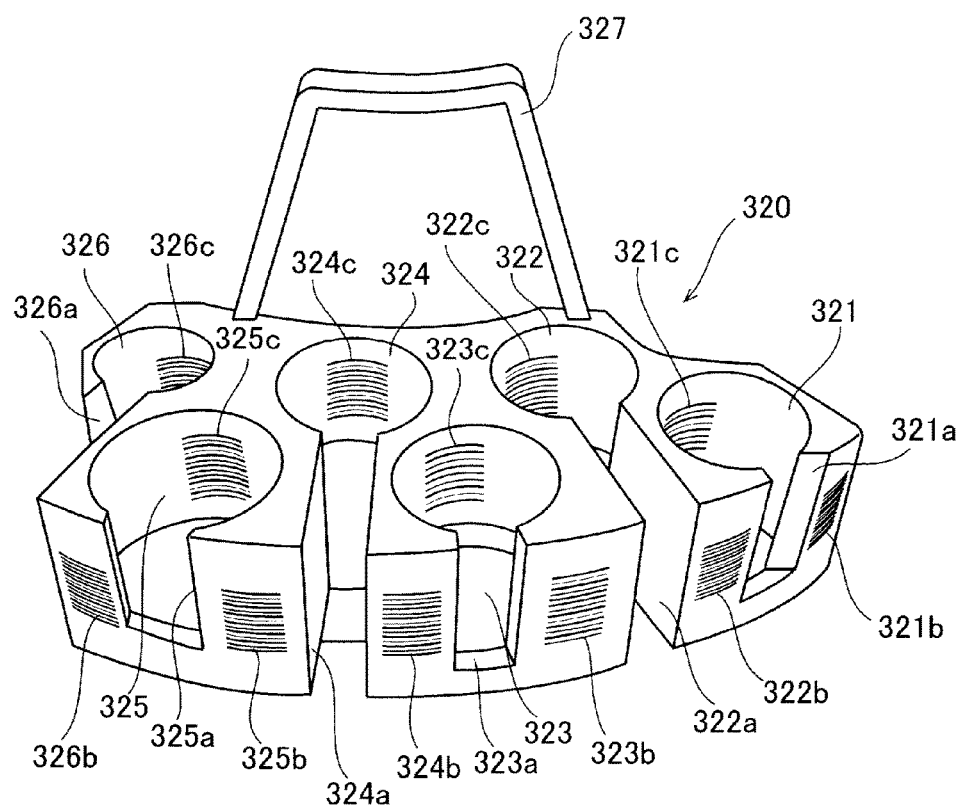
FIG. 14 is a perspective view showing a second reagent container rack according to one embodiment.

As shown in FIG. 5, five second reagent container racks 320 can be arranged in the second reagent table 12. The reagent containers 300 are arranged in a circular ring form in these five second reagent container racks 320. One of the five gaps of the second reagent container rack 320 adjacent to each other has a spacing larger than the spacing of the other four gaps. The barcodes 311b and 312b of the first reagent container rack 310 arranged in the first reagent table 11 positioned on the inner side of the second reagent table 12 and the barcode 300a of the reagent container 300 held by the first reagent container rack 310 are read by the barcode reader 350 positioned exterior to the reagent storing section 6 by way of a gap 12a having the large spacing. As shown in FIGS. 14 and 16, the second reagent container rack 320 includes six holding parts 321 to 326 for holding the reagent container 300, cut-out portions 321a to 326a respectively arranged on the front face side of the holding parts 321 to 326, and one gripping part 327 arranged so as to project upward. Moreover, the holding parts 321 to 326 of the second reagent container rack 320 are formed into a circular form in plan view, similar to the first reagent container rack 310, and are able to hold the reagent container 300 when the reagent container 300 of cylindrical shape is inserted thereto. The second reagent container rack 320 includes three types of racks formed so that the combination of the inner diameters of the holding parts 321 to 326 is different. The reagent same as the reagent arranged in the first reagent container rack 310 can be arranged in the second reagent container rack 320.

Barcodes 321b and 322b are respectively arranged on both sides of the cut-out portion 321a on the front column side. Similarly, barcodes 323b and 324b as well as barcodes 325b and 326b are respectively arranged on both sides of the cut-put portion 323a and on both sides of the cut-out portion 325a. Barcodes 321c to 326c are respectively arranged on the inner surface of the holding parts 321 to 326.

Each barcode 321b to 326b include positional information (holder number) for identifying the position of the holding parts 321 to 326. The barcodes 321c and 326c include information (no reagent container information) indicating that the reagent container 300 held by the holding parts 321 to 326 does not exist.

Furthermore, the reagent information or no reagent container information read by the barcode reader 350 are stored in a hard disc 401d of the control section 4a in correspondence to the positional information (holder number). The information stored in the hard disc 401d is reflected on the reagent managing screen 410 of the display device 4b by the control section 4a of the control device 4.

The barcodes 311b, 312b and 321b to 326b show four digit values. The first digit takes a value of "A" or "B", where "A" indicates that the reagent container 300 is arranged in the second reagent table 12, and "B" indicates that the reagent container 300 is arranged in the first reagent table 11. The second digit takes a value between "1" to "5", where "1" to "3" each indicates the shape of the three types of the second reagent container rack 320, and "4" and "5" each indicates the shape of the two types of the first reagent container rack 310. The third digit takes a value between "0" to "9" and indicates the number of the first reagent container rack 310 or the second reagent container rack 320. The fourth digit takes a value of "1" or "2" in the barcodes 311b and 312b of the first reagent container rack 310, where "1" and "2" indicates the holding part 311 and 312, respectively. The fourth digit takes a value between "1" and "6" in the barcodes 321b to 326b of the second reagent container rack 320, where "1" to "6" respectively indicates the holding parts 321 to 326. The value of the barcode (barcodes 311b, 312b and 321b to 326b) is reflected on the position displaying part 421a of the first reagent mark 421, the position displaying part 422a of the second reagent mark 422, or the position displaying part 427a of the reagent non-arranged mark 427 of the reagent managing screen 410, as shown in FIG. 7. For example, if the value of the barcode is "A11-6", this represents the sixth holding part (holding part 326) of the second reagent container rack 320 of rack number 1 in the rack (second reagent container rack 320) corresponding to "1" of the three types arranged in the second reagent table 12. That is, the first three digits of the four digit values specify the reagent container rack, and the last one digit specifies the position of the reagent in the reagent container rack.

The reagent name of the detailed information is reflected on the reagent name displaying parts 421b and 422b of the first reagent mark 421 and the second reagent mark 422 of the reagent managing screen 410. The no reagent container information is reflected to the reagent non-arranged mark 427. As shown in FIG. 7, the reagent name is displayed on the reagent name displaying part 421b or 422b if the reagent is arranged, and nothing will be displayed on the reagent name displaying part 421b or 422b if the reagent is not arranged. For example, the reagent name "CaC12" is arranged in the reagent position "A12-5", and the reagent is not arranged in the reagent position "A14-2".

As shown in FIGS. 1 and 2, the reagent replacing section 7 is arranged in the vicinity of the central part of the sample analyzer 1. In the present embodiment, the reagent replacing section 7 includes detachable first lid 30 and second lid 40 including a lock mechanism 31 and 41, respectively, and a notifying part 50 for notifying the conveyance state of the first reagent table 11 and the second reagent table 12 to the user, as shown in FIG. 3.

The first lid 30 is adapted so as to be detached when replacing the reagent container 300 arranged in the first reagent table 11 (first reagent container rack 310). The lock mechanism 31 of the first lid 30 is arranged to lock the first lid 30 so as not to detach in time of normal use or after replacement or addition of the reagent is finished and to have the control section 4a recognize that replacement or addition of the reagent in the first reagent table 11 is finished.

The second lid 40 is adapted so as to be detached when replacing the reagent container 300 arranged in the second reagent table 12 (second reagent container rack 320). The lock mechanism 41 of the second lid 40 is arranged to lock the second lid 40 so as not to detach in time of normal use or after replacement or addition of the reagent is finished and to have the control section 4a recognize that replacement or addition of the reagent in the second reagent table 12 is finished.

The notifying part 50 includes two LED indicators 51 and 52. As shown in FIGS. 1 and 3, the two LED indicators 51 and 52 are arranged in the vicinity of the second lid 40, and are visible by the user from outside the sample analyzer 1. The LED indicators 51 and 52 can emit light in blue or red.

The LED indicator 51 has a function of notifying the user that the first reagent container rack 310 corresponding to the reagent of the first reagent table 11 specified by the user in the reagent managing screen 410 has moved to a retrieving position (below the first lid 30) at where the reagent can be replaced. Specifically, the LED indicator 51 is configured to emit a red light while the first reagent table 11 is rotatably moving, and to emit a blue light when the first reagent container rack 310 corresponding to the reagent of the specified first reagent table 11 is moved to the retrieving position and stopped. Thus the timing of detaching the first lid 30 to replace or add the reagent can be notified to the user.

The LED indicator 52 has a function of notifying the user that the second reagent container rack 320 corresponding to the reagent of the second reagent table 12 specified by the user in the reagent managing screen 410 has moved to a retrieving position (below the second lid 40) at where the reagent can be replaced. Similar to the LED indicator 51, the LED indicator 52 is configured to emit a red light while the second reagent table 12 is rotatably moving, and to emit a blue light when the second reagent container rack 320 corresponding to the reagent of the specified second reagent table 12 is moved to the retrieving position and stopped.

The sample analyzer 1 is configured such that the reading of the barcode 300a of all the reagent containers 300 held in the first reagent container rack 310 or the second reagent container rack 320 holding the replaced reagent is automatically performed after the user locks the first lid 30 or the second lid 40 when the replacement or addition of the reagent is finished. When reagents other than the specified reagent contained in the same first reagent container rack 310 or the second reagent container rack 320 is replaced in addition to the specified reagent when one reagent is specified and the replacement of the reagent is instructed, the arrangement of the reagents after the replacement is correctly reflected on the reagent managing screen 410.

Furthermore, as shown in FIGS. 3 to 5, the measurement mechanism unit 2 includes a cuvette conveying section 60, the specimen dispensing arm 70, the first optical information acquiring section 80, a lamp unit 90, a warming section 100, a cuvette transporting section 110, the reagent dispensing arm 120, the second optical information acquiring section 130, the urgent specimen setting section 140, a fluid section 150, and a cuvette supply mechanism section 160.

The cuvette conveying section 60 has a function of conveying the cuvette 200 to each section of the sample analyzer 1. The cuvette conveying section 60 includes a cuvette conveying table 61 of circular ring shape arranged on the outer side of the second reagent table 12 of circular ring shape, and a plurality of cylindrical shaped cuvette holding parts 62 arranged at a predetermined interval along the circumferential direction on the cuvette conveying table 61. The cuvette holding part 62 is arranged to hold the cuvette 200 one by one. The specimen accommodated in the test tube 250 of the conveyance mechanism unit 3 and the reagent held in the reagent holding section 6 are dispensed into the cuvette 200 (see FIG. 5) held in the cuvette holding part 62 of the cuvette conveying table 61 to prepare the measurement sample.

The specimen dispensing arm 70 has a function of suctioning the specimen accommodated in the test tube 250 conveyed to the suction position 2a by the conveyance mechanism unit 3, and dispensing the suctioned specimen into the cuvette 200 held by the cuvette holding part 62 of the cuvette conveying table 61.

The first optical information acquiring section 80 is configured to acquire optical information from the specimen to measure the presence and the concentration of interfering substances (milky fluid (fat), hemoglobin, and bilirubin) in the specimen before the reagent is added. Specifically, the presence and the concentration of the interfering substance are measured using four types of light (405 nm, 575 nm, 660 nm, and 800 nm) out of the five types of light (340 nm, 405 nm, 575 nm, 660 nm, and 800 nm) irradiated from the lamp unit 90 to be hereinafter described. The light having a wavelength of 405 nm is light that is absorbed by any one of milky fluid, hemoglobin, and bilirubin. That is, the influence of milky fluid, hemoglobin, and bilirubin contributes to the optical information measured by the light having the wavelength of 405 nm. The light having a wavelength of 575 nm is light that is not substantially absorbed by bilirubin but is absorbed by milky fluid and hemoglobin. That is, influence of milky fluid and hemoglobin contributes to the optical information measured by the light having the wavelength of 575 nm. The light having a wavelength of 660 nm and 800 nm are light that are not substantially absorbed by bilirubin and hemoglobin but are absorbed by milky fluid. That is, influence of milky fluid contributes to the optical information measured by the light having the wavelength of 660 nm and 800 nm. The milky fluid absorbs the light having the wavelength from 405 nm of low wavelength region up to 800 nm of high wavelength region, and the light having the wavelength of 660 nm is more absorbed by the milky fluid than the light having the wavelength of 800 nm. That is, the influence of the milky fluid is small in the optical information measured by the light having the wavelength of 800 nm than in the optical information measured by the light having the wavelength of 660 nm.

The acquisition of the optical information of the specimen by the first optical information acquiring section 80 is performed prior to the optical measurement (actual measurement) of the specimen by the second optical information acquiring section 130. The first optical information acquiring section 80 acquires optical information (information by transmitted light of the specimen) from the specimen in the cuvette 200 held by the cuvette holding part 62 of the cuvette conveying table 61.

Furthermore, the first optical information acquiring section 80 is electrically connected to the control section 4a of the control device 4, and transmits the data (optical information) acquired by the first optical information acquiring section 80 to the control section 4a of the control device 4. Thus, analysis of the data from the first optical information acquiring section 80 is carried out in the control device 4, so that the absorbance of the specimen in the cuvette 200 with respect to the five types of light exited from a branched optical fibers 91 is obtained, and the presence and the concentration of the interfering substances in the specimen etc. are analyzed. In the present embodiment, judgment is made on whether or not to analyze the optical information measured in the second optical information acquiring section 130, to be hereinafter described, based on the presence and the concentration of the interfering substances in the specimen.

As shown in FIG. 5, the lamp unit 90 is arranged to provide light (340 nm, 405 nm, 575 nm, 660 nm, and 800 nm) having five types of wavelength used in the optical measurement performed in the first optical information acquiring section 80 and the second optical information acquiring section 130. That is, one lamp unit 90 is configured to be commonly used for the first optical information acquiring section 80 and the second optical information acquiring section 130. The light of the lamp unit 90 is provided to the first optical information acquiring section 80 and the second optical information acquiring section 130 by the branched optical fiber 91 and the branched optical fiber 92, respectively.

The warming section 100 includes a plate 101 that can be heat-retained, and is arranged with ten concave shaped cuvette holding parts 101a. Each cuvette holding part 101a is capable of holding one cuvette 200, and has a function of warming the specimen in the cuvette 200 to about 37° C. by holding the cuvette 200 dispensed with the specimen for a few minutes in the cuvette holding part 101a. The specimen warmed by the warming section 100 is dispensed with reagent and subjected to measurement within a constant time after warming is finished. The alteration of the specimen, and the measurement sample prepared from the specimen and the reagent is suppressed, and the measurement result stabilizes.

The cuvette transporting section 110 is arranged to transport the cuvette 200 among the cuvette conveying section 60, the warming section 100, and the second optical information acquiring section 130. The cuvette transporting section 110 includes a transport catcher part 111 for gripping the cuvette 200 and a driving part 112 for moving the transport catcher part 111. The transport catcher part 111 is movable in the moving region 110a by the drive of the driving part 112, and transports the cuvette 200 among the cuvette conveying section 60, the warming section 100, and a measurement mounting part 131 of the second optical information acquiring section 130. A vibrating function is provided to the transport catcher part 111, whereby the specimen and the reagent in the cuvette 200 can be stirred by vibrating the cuvette 200 while gripping the cuvette 200.

As shown in FIGS. 3 to 5, the reagent dispensing arm 120 is arranged to mix the reagent with the specimen in the cuvette 200 by dispensing the reagent in the reagent container 300 placed in the reagent storing section 6 into the cuvette 200. Specifically, suction of the reagent is performed through holes 22a, 22b, or 22c (see FIG. 3) in the outer wall part 20 of the reagent storing section 6, and the transport catcher part 111 takes out the cuvette 200 in which warming (37° C.) is completed from the cuvette holding part 101a of the warming section 100 and dispenses the suctioned reagent into the cuvette 200 in a gripping state. A warming function is provided to a pipette part 121 of the reagent dispensing arm 120, and the suctioned reagent is instantaneously warmed to about 37° C. That is, the low temperature (about 10° C.) stored reagent in the reagent storing section 6 is mixed with the specimen of about 37° C., which warming is completed, while being warmed to about 37° C. by the reagent dispensing arm 120. Therefore, the reagent is added to the specimen completed with optical measurement by the first optical information acquiring section 80 to prepare the measurement sample.

In the present embodiment, the reagent dispensing arm 120 is configured to move the pipette part 121 in the up and down direction through pulse control by a stepping motor (not shown) when performing the dispensing operation. A sensor (not shown) for detecting the fluid level of the reagent when suctioning the reagent from the reagent container 300 is arranged at the distal end of the pipette part 121 of the reagent dispensing arm 120. Thus, the height of the fluid level of the reagent in the reagent container 300 can be calculated by the number of pulse until the fluid level of the reagent is detected, and the movement amount for one pulse. The procedures for calculating the height of the fluid level of the reagent will be hereinafter described in detail.

In the present embodiment, when replacement of the reagent is instructed during the operation of the reagent dispensing arm 120, the dispensing task of the reagent to be dispensed by the reagent dispensing arm 120 from the reagent table containing the specified reagent is stopped if the dispensing task of the reagent to be dispensed is carried out from the reagent table containing the specified reagent. In this case, if the reagent to be dispensed is also contained in the reagent table different from the reagent table containing the specified reagent, the reagent dispensing arm 120 stops the dispensing task of the reagent to be dispensed of the reagent table containing the specified reagent, and continues the dispensing task from the reagent to be dispensed contained in the other reagent table. If the reagent to be dispensed is arranged only in the reagent table containing the reagent instructed to be replaced, the reagent dispensing arm 120 is configured so as not to perform the dispensing operation after finishing the dispensing of the reagent to be dispensed with respect to the specimen (specimen waiting to be dispensed with reagent) being warmed in the warming section 100 in time of replacement instruction. Therefore, the measurement is performed within a constant time after warming even for the specimen that is being warmed in the warming section 100 in time of replacement instruction.

The second optical information acquiring section 130 has a function of measuring optical information from the measurement sample. As shown in FIG. 5, the second optical information acquiring section 130 is configured by a measurement mounting part 131 and a detecting part 132 arranged below the measurement mounting part 131.

The detecting part 132 of the second optical information acquiring section 130 is configured so as to perform optical measurement (actual measurement) under a plurality of conditions on the measurement sample in the cuvette 200. The second optical information acquiring section 130 is electrically connected to the control section 4a of the control device 4 and transmits the acquired data (optical information) to the control section 4a of the control device 4. In the control device 4, the data (optical information) transmitted from the second optical information acquiring section 130 is analyzed based on the result of analysis of the data (optical information) from the first optical information acquiring section 80 acquired in advance, and displayed on the display device 4b.

The light having the wavelength 660 nm irradiated from the branched optical fiber 92 is the main wavelength used in measuring Fbg (Fibrinogen content), PT (prothrombin time), and APTT (activated partial thromboplastin time). The light having the wavelength of 800 nm is the sub-wavelength used in measuring as Fbg, PT, and APTT. The measuring wavelength of ATIII, which is the measurement item of synthetic substrate method, is 405 nm, and the measuring wavelength of D dimmer and FDP, which are the measurement items of immunoturibidmetric method, is 800 nm. The measuring wavelength of the platelet agglutination method is 575 nm.

As shown in FIGS. 3 to 5, the urgent specimen setting section 140 is arranged to perform specimen analyzing process on the urgent specimen. The urgent specimen setting section 140 is configured to cut the urgent specimen in when the specimen analyzing process is being performed on the specimen supplied from the conveyance mechanism unit 3. The urgent specimen setting section 140 is slidable in the X direction and is arranged with five holding parts 141 for holding the container (not shown) accommodating diluting fluid and cleaning fluid. A barcode (not shown) is attached to the container (not shown) accommodating the diluting fluid and the cleaning fluid. The barcode of the diluting fluid and the cleaning fluid is configured so as to be read by the barcode reader 351 while the urgent specimen setting section 140 is being slid in the X direction. Thus, the type, arrangement, and the like of the diluting fluid and the cleaning fluid are displayed as a diluting/cleaning fluid mark 423 of the reagent managing screen 410. As shown in FIGS. 1 and 2, a lid 1c is arranged on the front face side of the replacing section 7 of the sample analyzer 1. The replacement or addition of the container (not shown) accommodating the diluting fluid and the cleaning fluid is performed through the lid 1c.

The fluid section 150 is arranged to supply fluid such as cleaning fluid to the nozzle arranged in each dispensing arm (specimen dispensing arm 70 and reagent dispensing arm 120) in the shut-down process of the sample analyzer 1.

The cuvette supply mechanism section 160 is configured to sequentially supply the plurality of cuvettes 200 randomly placed by the user to the cuvette conveying section 60. As shown in FIGS. 3 to 5, the cuvette supply mechanism section 160 includes a first hopper 161a, a second hopper 161b supplied with the cuvette 200 from the first hopper 161a and being smaller than the first hopper 161a; two induction plates 162 supplied with the cuvette 200 from the second hopper 161b; a supporting table 163 arranged on the lower end of the two induction plates 162; and a supply catcher part 164 arranged at a predetermined distance from the supporting table 163. The cuvette 200 supplied to the first hopper 161a is slidably moved towards the supporting table 163 on the induction plates 162 by way of the second hopper 161b which is smaller than the first hopper 161a. The supporting table 163 rotatably transports the cuvette 200 slidably moved on the induction plates 162 to a position allowing the supply catcher part 164 to grip the cuvette 200. The supply catcher section 164 is arranged to supply the cuvette 200 rotatably transported by the supporting table 163 to the rotation conveying section 60.

Furthermore, as shown in FIGS. 3 to 5, a discarding hole 171 (see FIGS. 3 and 5) for discarding the cuvette 200 and a discarding box 172 arranged under the discarding hole 171 are arranged at a predetermined spacing from the supply catcher part 164 described above in the measurement mechanism unit 2. The supply catcher part 164 described above can discard the cuvette 200 on a cuvette conveying table 61 of the cuvette conveying section 60 to the discarding box 172 through the discarding hole 171 (see FIGS. 3 and 5). That is, the supply catcher part 164 performs both supply and discard of the cuvette 200.

The specimen analyzing operation of the sample analyzer 1 will now be described in detail with reference to FIGS. 4 and 5. The operation in the measurement using coagulation time will be described herein.

First, the power of the measurement mechanism unit 2 and the control device 4 of the sample analyzer 1 shown in FIG. 4 are turned ON to perform the initial setting of the sample analyzer 1. The operation for returning the mechanisms for moving the cuvette 200 and each dispensing arm (specimen dispensing arm 70 and reagent dispensing arm 120) to the respective initial positions, initialization of the software stored in the control section 4a of the control device 4, and the like are thereby performed.

The rack 251 mounted with the test tube 250 accommodating the specimen is conveyed by the conveyance mechanism unit 3 shown in FIG. 5. The rack 251 in the rack set region 3a is thereby conveyed to the position corresponding to the suction position 2a of the measurement mechanism unit 2.

A predetermined amount of specimen is suctioned from the test tube 250 by the specimen dispensing arm 70. The specimen dispensing arm 70 is moved above the cuvette 200 held at the cuvette conveying table 61 of the cuvette conveying section 60. Thereafter, the specimen is discharged into the cuvette 200 of the cuvette conveying table 61 from the specimen dispensing arm 70, and the specimen is sorted in the cuvette 200.

The cuvette conveying table 61 is then rotated to convey the cuvette 200 dispensed with the specimen to the position at where measurement can be performed by the first optical information acquiring section 80. The optical measurement is thus carried out on the specimen by the first optical information acquiring section 80, and optical information is acquired from the specimen. Specifically, the electric signal data from five types (340 nm, 405 nm, 575 nm, 660 nm, and 800 nm) of light transmitted through the specimen in the cuvette 200 held in the cuvette holding part 62 (see FIG. 5) of the cuvette conveying table 61 are transmitted to the control section 4a of the control device 4. The acquisition of optical information (first optical information) on the specimen by the first optical information acquiring section 80 is thereby completed.

The control section 4a of the control device 4 calculates the absorbance of the specimen using the received data (first optical information) and calculates the presence and concentration of the interfering substances (milky fluid, hemoglobin, bilirubin) in the specimen. Specifically, the control section 4a of the control device 4 calculates the absorbance of the specimen based on the optical information (first optical information) acquired using four types (405 nm, 575 nm, 660 nm, and 800 nm) of light irradiated from the lamp unit 90, and stores the absorbance in the RAM 401c.

Subsequently, determination is made on whether or not the absorbance at the main wavelength out of the absorbance stored in the RAM 401c is lower than or equal to the threshold value. Specifically, in the case where the examining items of the specimen are the examining items of the coagulation time method such as "PT", "APTT", "Fbg" etc., determination is made on whether or not the absorbance calculated from the first optical information measured by irradiating the light having the wavelength 660 nm, which is the main wavelength for the relevant items, is lower than or equal to a threshold value (e.g., 2.0).

If the absorbance at the main wavelength calculated from the first optical information measured in the first optical information acquiring section 80 is lower than or equal to the threshold value, the cuvette 200 is transported to the warming section 100 from the cuvette conveying table 61 by the cuvette transporting section 110. The cuvette 200 accommodating the specimen which is made to about 37° C. in the warming section 100 is then gripped by the transport catcher part 111 of the cuvette transporting section 110. With the cuvette 200 gripped by the transport catcher part 111, the reagent dispensing arm 120 is driven, and the reagent in the reagent container 300 placed on the reagent table (first reagent table 11 or second reagent table 12) is added to the specimen in the cuvette 200. In this state, the specimen and the reagent in the cuvette 200 are stirred by the vibrating function of the transport catcher part 111. The measurement sample is thereby prepared. The cuvette 200 accommodating the measurement sample is then moved as it is to the measurement mounting part 131 of the second optical information acquiring section 130 by the cuvette transporting section 110.

The optical information (second optical information) is acquired from the measurement sample by performing the optical measurement (actual measurement) under the plurality of conditions on the measurement sample in the cuvette 200 by the detecting part 132 of the second optical information acquiring section 130. Specifically, the light from the branched optical fiber 92 of the lamp unit 90 is first irradiated on the cuvette 200 of the measurement mounting part 131. Lights having five different wavelengths (340 nm, 405 nm, 575 nm, 660 nm, and 800 nm) are irradiated from the branched optical fiber 132. The electric signal data corresponding to the light of each wavelength irradiated from the branched optical fiber 92 and transmitted through the cuvette 200 and the measurement sample in the cuvette 200 are then acquired.

The electric signal data corresponding to the light having five different wavelengths are sequentially transmitted to the control section 4a of the control device 4. The acquisition of the optical information (second optical information) on the measurement sample by the second optical information acquiring section 130 is thereby completed.

If the absorbance at the main wavelength calculated from the first optical information measured in the first optical information acquiring section 80 is greater than the threshold value, determination is made on whether or not the absorbance at the sub-wavelength calculated from the first optical information measured in the first optical information acquiring section 80 is lower than or equal to a threshold value. Specifically, in the case where the examining items of the specimen are examining items of the coagulation time method such as "PT", "APTT", "Fbg" and the like, determination is made on whether or not the absorbance calculated from the first optical information measured by irradiating the light having the wavelength 800 nm, which is the sub-wavelength for the relevant items, is lower than or equal to a threshold value (e.g., 2.0).

If the absorbance at the sub-wavelength calculated from the first optical information measured in the first optical information acquiring section 80 is lower than or equal to the threshold value, the optical information (second optical information) on the measurement sample is acquired by the second optical information acquiring section 130.

If the absorbance at the sub-wavelength calculated from the first optical information measured in the first optical information acquiring section 80 is greater than the threshold value, the analysis of high reliability is judged as difficult to conduct since the influence of the interfering substances (milky fluid, hemoglobin, bilirubin) in the specimen is large, and the actual measurement is canceled. The reagent cannot be added to the non-analyzable specimen significantly influenced by the interfering substances and the measurement sample cannot be prepared, and thus the reagent is suppressed from becoming a waste. A situation where measurement of high reliability is difficult to conduct (when canceling the actual measurement) includes a case where the light transmitting through the specimen is shielded due to the presence of a great amount of interfering substances in the specimen detected in the first optical information acquiring section 80, and the transmitted light that has transmitted through the specimen cannot be substantially detected.

After the acquisition (actual measurement) of the second optical information by the second optical information acquiring section 130 described above, the second optical information of the measurement sample measured at the main wavelength out of the plurality of second optical information measured in the second optical information acquiring section 130 is transmitted to the control section 4a of the control device 4, and is analyzed by the application program 404a installed in the hard disc 401d of the control section 4a. For instance, when the examining item of the specimen is "PT", the second optical information measured by irradiating the light having a wavelength of 660 nm, which is the main wavelength of "PT", is transmitted to the control section 4a of the control device 4. Thereafter, the control section 4a that has received the second optical information acquired at the main wavelength outputs the result of analysis based on the second optical information.

Similarly, after the acquisition (actual measurement) of the second optical information by the second optical information acquiring section 130, the second optical information of the measurement sample measured at the sub-wavelength out of the plurality of second optical information measured in the second optical information acquiring section 130 is transmitted to the control section 4a of the control device 4, and is analyzed by the application program 404a installed in the hard disc 401d of the control section 4a. For instance, when the examining item of the specimen is "PT", the second optical information measured by irradiating the light having a wavelength of 800 nm, which is the sub-wavelength of "PT", is transmitted to the control section 4a of the control device 4. Thereafter, the control section 4a that has received the second optical information acquired at the sub-wavelength outputs the result of analysis based on the second optical information.

After the analysis by the control section 4a of the control device 4 is finished, the obtained result of analysis is displayed on the display device 4b of the control device 4. The analyzing operation of the specimen of the sample analyzer 1 is thereby terminated.

Figure 27:
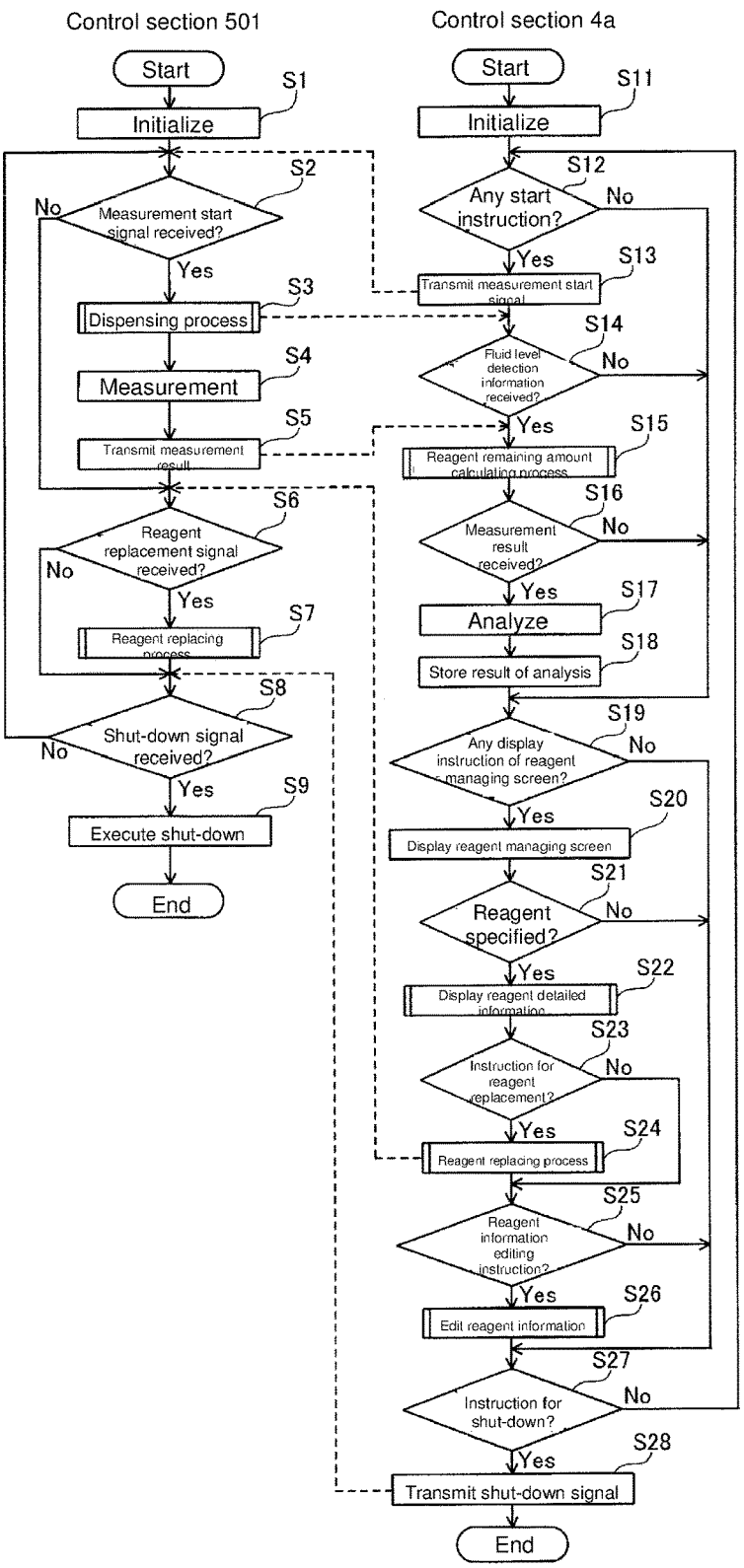
FIG. 27 is a flowchart describing the measurement process by the control section of the control device and the control section of the measurement mechanism unit of the sample analyzer according to one embodiment of the present invention.

FIG. 27 is a flowchart describing the measurement process flow of the control section 4a of the control device 4 and the control section 501 of the measurement mechanism unit 2 of the sample analyzer 1 according to the present embodiment. The measurement flow process of the control section 4a and the control section 501 of the sample analyzer 1 according to the present embodiment will now be described with reference to FIGS. 1, 3, 7, and 27.

First, the power (not shown) of the measurement mechanism unit 2 is turned ON, so that initialization of the control section 501 (initialization of the program) is executed and the operation check of each section of the measurement mechanism unit 2 is performed in step S1. The power (not shown) of the control device 4 is then turned ON, so that initialization of the control section 4a (initialization of the program) is executed in step S11. After initialization of the control section 501 is completed, the control section 501 requests an initialization completed signal indicating the completion of initialization of the control section 4a, and after receiving such initialization completed signal, controls the barcode reader 350 so that the barcodes of all the reagents set in the reagent storing section 6 and the barcodes of the reagent rack are read. The read barcode information is transmitted from the control section 501 to the control section 4a, and stored in the hard disc 401d of the control section 4a.

In step S12, a menu screen (not shown) is displayed on the display device 4b, where the user pushes the start button displayed on the menu screen to transmit a measurement start signal from the control section 4a to the control section 501 in step S13. If the start button is not pushed in step S12, the process proceeds to step S19.

In step S2, judgment is made on whether or not the measurement start signal is received by the control section 501, where the process proceeds to step S3 if judged that the measurement start signal is received, and the process proceeds to step S6 if judged that the measurement start signal is not received.

In step S3, the process of dispensing the reagent to the specimen dispensed in the cuvette 200 is performed, and detection of the fluid level is performed when suctioning the reagent to acquire the fluid level detection information, and such fluid level detection information is transmitted from the control section 501 to the control section 4a. In step S4, measurement of the specimen dispensed with the reagent is performed in the first optical information acquiring section 80 and the second optical information acquiring section 130, and in step S5, the measurement result is transmitted from the control section 501 to the control section 4a.

In step S14, judgment is made on whether or not the fluid level detection information is received by the control section 4a, where the process proceeds to step S15 if the fluid level detection information is received, and the process proceeds to step S19 if the fluid level detection information is not received. In step S15, the reagent remaining amount calculating process is performed by the control section 4a. The reagent remaining amount calculating process will be hereinafter described, but is a process of calculating the remaining amount of reagent based on the fluid level detection information and storing the remaining amount of reagent in the hard disc 401d.

In step S16, judgment is made on whether or not the measurement result is received by the control section 4a, where the process proceeds to step S17 if the measurement result is received, and the process proceeds to step S19 if the measurement result is not received. In step S17, the measurement result is analyzed by the control section 4a, and in step S18, the result of analysis is stored in the hard disc 401d.

In step S19, judgment is made on whether or not instruction to display the reagent managing screen 410 is made by the control section 4a (whether or not the reagent button (not shown) for displaying the reagent managing screen 410 of the menu screen is pushed), where the process proceeds to step S20 if such display instruction of the reagent managing screen 410 is made, and the process proceeds to step S27 if the display instruction of the reagent managing screen 410 is not made. In step S20, the reagent managing screen 410 is displayed by the control section 4a. When the reagent managing screen 410 is displayed, information necessary for the first reagent mark 421, the second reagent mark 422, and the reagent detailed information displaying region 430 are reflected based on the read barcode information (step S1) and the calculated reagent remaining amount (step S15) by the control section 4a (see FIG. 7). The remaining amount of the reagent is displayed on the remaining amount indicator 421c of the first reagent mark 421 and the remaining amount indicator 422c of the second reagent mark 422 displayed on the reagent arrangement displaying region 420 of the reagent managing screen 410. There are three types of calculated reagent remaining amount to be hereinafter described, the first reagent remaining amount, the second reagent remaining amount, and the third reagent remaining amount. The remaining amount indicator is displayed in red for the first reagent remaining amount, the remaining amount indicator is displayed in yellow for the second reagent remaining amount, and the remaining amount indicator is not displayed for the third reagent remaining amount.

In step S21, judgment is made on whether or not the reagent to be replaced is specified by the control section 4a in the reagent managing screen 410 of the display device 4b having a touch panel mechanism. The details on specifying the reagent will be described below. The user first references the reagent arrangement displaying region 420 of the reagent managing screen 410 shown in FIG. 7 to check the arrangement of the reagents. The user also specifies an arbitrary reagent by directly touching by hand the first reagent mark 421 or the second reagent mark 422 where the reagent is displayed from the plurality of first reagent marks 421 or the second reagent marks 422, and checks the detailed information of the specified reagent displayed on the reagent detailed information displaying region 430. The background color (e.g., blue (with hatching (diagonal lines) in FIG. 7)) of the reagent name displaying part of the specified reagent mark "SHP" is displayed so as to be different from the background color (e.g., white (without hatching (diagonal lines) in FIG. 7)) of the reagent name displaying part of the reagent mark other than the reagent mark "SHP". After the user determines the reagent to be replaced, the user specifies the first reagent mark 421 or the second reagent mark 422 where the reagent to be replaced is displayed. If judged that the reagent is specified by the control section 4a in step S21, the process proceeds to step S22, and if judged that the reagent is not specified, the process proceeds to step S27.

In step S22, the reagent detailed information displaying process in which the reagent detailed information of the specified reagent is displayed on the reagent detailed information display region 430 is performed, and in step S23, judgment is made on whether or not instruction for reagent replacement is made (whether or not replacement/addition button 440a is pushed) by the control section 4a. In FIG. 7, the reagent "SHP" of the reagent position "A11-6" is specified, and the detailed information of the reagent "SHP" is displayed on the reagent detailed information displaying region 430. If judged that instruction for reagent replacement is made in step S23, the reagent replacing process is performed by the control section 4a and the reagent replacement signal is transmitted from the control section 4a to the control section 501 in step S24. If judged that instruction for reagent replacement is not made in step S23, the process proceeds to step S25.

In step S25, judgment is made on whether or not editing instruction of the reagent information is made by the control section 4a, where the process proceeds to step S26 if the editing instruction of the reagent information is made, and the process proceeds to step S27 if the editing instruction for the reagent information is not made. In step S26, the editing process of the reagent information is carried out by the control section 4a.

In step S27, judgment is made on whether or not instruction for shut-down is made (whether or not shut-down button (not shown) is pushed from the menu screen) by the control section 4a, where the process proceeds to step S28 if judged that the instruction for shut-down is made, and the process returns to step S12 if judged that the instruction for shut-down is not made. In step S28, the shut-down signal is transmitted from the control section 4a to the control section 501, the shut-down of the control device 4 is carried out, and the process is terminated.

In step S6, judgment is made on whether or not the reagent replacement signal is received by the control section 501, where the process proceeds to step S7 if judged that the reagent replacement signal is received, and the process proceeds to step S8 if judged that the reagent replacement signal is not received. In step S7, the reagent replacing process is carried out by the control section 501.

In step S8, judgment is made on whether or not the shut-down signal is received, where the process proceeds to step S9 if judged that the shut-down signal is received, and the process returns to step S2 if judged that the shut-down signal is not received. In step S9, the shut-down of the measurement mechanism unit 2 is executed, and the process is terminated.

In the measurement process flow of the control section 501, step S3, step S4, and step S7 are parallel processed. Furthermore, in the measurement process flow of the control section 4a, step S15, step S17, step S20, step S22 and step S26, and step S24 are parallel processed.

Figure 19:
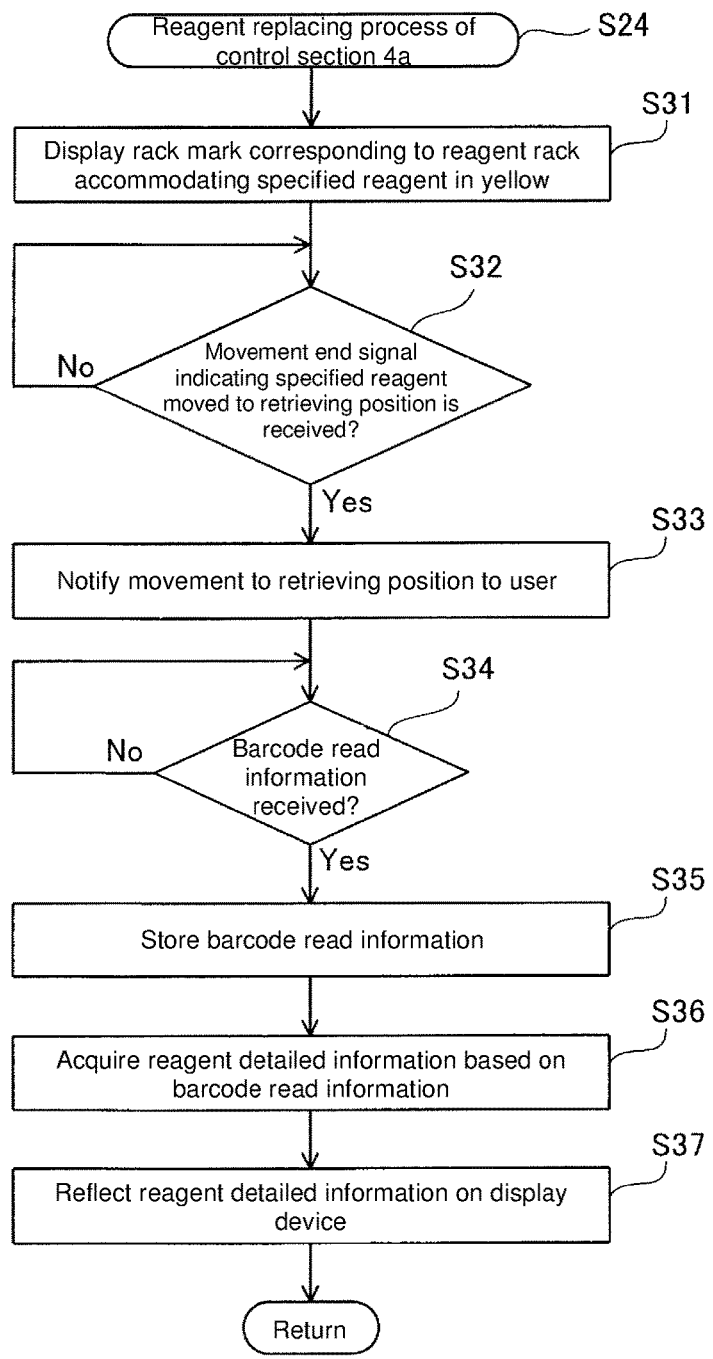
FIG. 19 is a flowchart for explaining a reagent replacing process by the control section of the control device of the sample analyzer according to the one embodiment of the present invention.
Figure 20:
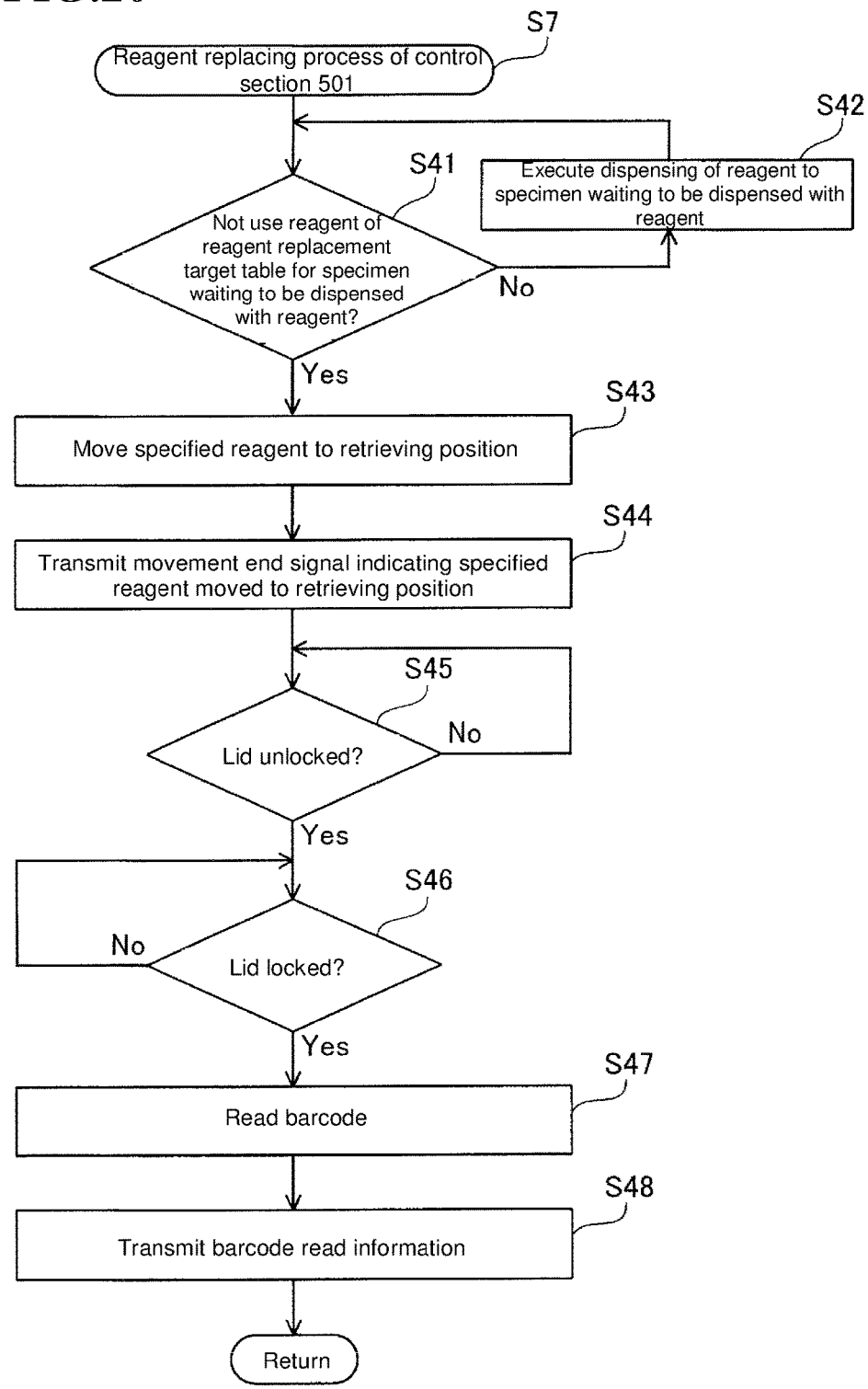
FIG. 20 is a flowchart for explaining a reagent replacing process by the control section of the measurement mechanism unit of the sample analyzer according to the one embodiment of the present invention.

FIG. 19 is a flowchart for describing the details of the reagent replacing process of the control section 4a executed in step S24 of the flowchart shown in FIG. 27. FIG. 20 is a flowchart for describing the details of the reagent replacing process of the control section 501 executed in step S7 of the flowchart shown in FIG. 27. The reagent replacing process flows of the control section 4a and the control section 501 of the reagent analyzer 1 according to the present embodiment will now be described with reference to FIGS. 3, 7 to 10, 19, and 20.

First, in step S31 shown in FIG. 19, the rack mark corresponding to the reagent container rack accommodating the specified reagent ("B11-2" of FIG. 8) is displayed in a predetermined color (e.g., yellow (illustrated in left diagonal hatching in FIG. 8)). With such display, the user can recognize that the reagent container rack accommodating the specified reagent is moving to the retrieving position. In the reagent replacing section 7, the LED indicator 51 or the LED indicator 52 emits a red light while the reagent container rack accommodating the specified reagent is moving to the retrieving position. An example of replacing the reagent "X1" of "B11-2" will be described herein.

In step S41 shown in FIG. 20, judgment is made on whether or not any of the specimen waiting to be dispensed with reagent described above uses the reagent of the reagent table (hereinafter referred to as reagent replacement target table) containing the rack holding the specified reagent by the control section 501, and if there is a specimen waiting to be dispensed with reagent that uses the reagent of the reagent replacement target table when receiving the reagent replacement signal, the dispensing of the reagent to the specimen is executed in step S42. All dispensing of the reagent from the reagent replacement target table to the specimen waiting to be dispensed with reagent that uses the reagent of the reagent replacement target table is performed by repeating step S41 and step S42. When there is a specimen that uses the reagent of the reagent replacement target table in the specimen waiting to be dispensed with reagent when instruction for reagent replacement is made, the reagent is dispensed to the relevant specimen before the execution of the reagent replacement. When the specimen is dispensed to the cuvette 200 and the measurement is started, the reagent must be dispensed to the relevant specimen after a predetermined time has elapsed, where the specimen cannot be used for the measurement unless such dispensing is properly performed, and thus must be discarded. Therefore, a predetermined process is performed on the specimen (specimen waiting to be dispensed with reagent) which measurement has started, and the measurement must be completed without being interrupted. If there is no specimen that uses the reagent of the reagent table of reagent replacement target in the specimen waiting to be dispensed with reagent when instruction for reagent replacement is made, the control section 501 executes the processes after step S43 and performs the reagent replacement operation. That is, in step S41, when there is no specimen waiting to be dispensed with reagent, or when the specimen uses the reagent of the reagent table none of which is reagent replacement target (even when there are any specimen waiting to be dispensed with reagent), the reagent replacement target table does not need to be accessed, and thus the reagent replacement operation is executed. Therefore, in both cases when there is specimen that uses the reagent of the reagent table of reagent replacement target in the specimen (specimen waiting to be dispensed with reagent) waiting to be dispensed with reagent when instruction for reagent replacement is made, and where there is no such specimen, the specimen waiting to be dispensed with reagent does not need to be discarded, and thus the specimen will not becomes a waste, and reagent replacement will be rapidly performed.

In step S41, if judged that all the specimens waiting to be dispensed with reagent do not use the reagent of the reagent table of reagent replacement target, the first driving section 502 or the second driving section 503 is controlled by the control section 501, and the reagent table of reagent replacement target rotates, so that the first reagent container rack 310 or the second reagent container rack 320 holding the specified reagent moves to the retrieving position (below first lid 30 or second lid 40) in step S43. In such process, the control section 501 issues a command to instruct the movement of the reagent replacement target table to the drive circuit. When the drive circuit receives such command, a reagent replacement flag of a status register incorporated in the drive circuit is set. In other words, the reagent replacement status described above is set to ON for the reagent replacement target table containing the reagent instructed to be replaced by the user. The reagent replacement status has either the reagent replacement status of the first reagent table 11 and the reagent replacement status of the second reagent table 12 set to ON. When the reagent container rack holding the specified reagent is moved to the retrieving position, a movement end signal indicating that the reagent container rack holding the specified reagent has moved to the retrieving position is transmitted to the control section 4a by the control section 501 in step S44. The amount of rotation movement of each reagent table 11, 12 from the origin position of the first reagent table 11 and the second reagent table 12 can be determined by counting the number of pulses of the drive pulse signal provided to the first driving section 502 or the second driving section 503 by the control section 501. The control section 501 thus recognizes that the first reagent table 11 or the second reagent table 12 has moved to the retrieving position by the movement amount from the origin position, and generates the movement end signal based on such recognition.

When the movement end signal is transmitted from the control section 501 to the control section 4a, judgment is made on whether or not the movement end signal is received by the control section 4a in step S32 shown in FIG. 19. If judged that the movement end signal is received in step S32, notification that the reagent container rack holding the specified reagent has moved to the retrieving position is made to the user in step S33. Specifically, the rack mark displayed in the predetermined color (e.g., yellow (illustrated in left diagonal hatching in FIG. 8)) in step S31 described above is displayed in a predetermined color (e.g., green (illustrated in right diagonal hatching in FIG. 9)) in the reagent managing screen 410. In the reagent replacing section 7, when the reagent container rack holding the specified reagent is moved to the retrieving position, the LED indicator 51 or the LED indicator 52 that emitted a red light during the movement of the reagent container rack now emits a blue light. The notification that the reagent container rack holding the specified reagent has moved to the retrieving position is thereby made to the user.

The lock mechanism of the lid of the table of reagent replacement target is unlocked by the user for the reagent replacement task. An unlock signal is transmitted from the lock detecting part of the lid to the control section 501, and judgment is made on whether or not the lock of the lid is unlocked by the control section 501 in step S45. Regarding the reagent replacement task by the user, after the first lid 30 or the second lid 40 in an unlocked state is detached by the user, the gripping part (gripping part 313 or 327) of the reagent container rack at the retrieving position (below first lid 30 or second lid 40) is gripped by the user and retrieved. The reagent container 300 accommodating the specified reagent is replaced with the reagent container 300 accommodating the new reagent by the user. Thereafter, the reagent container rack arranged with the replaced reagent is then returned to the retrieving position, and the user attaches and locks the first lid 30 or the second lid 40. A lock signal is transmitted from the lock detecting part of the lid to the control section 501, and judgment is made on whether or not the lid is locked by the control section 501 in step S46.

If judged that the first lid 30 or the second lid 40 is locked by the control section 501 in step S46, the barcode reading operation is performed in step S47. In the barcode reading operation, the control section 501 controls the first reagent table 11 or the second reagent table 12 and the barcode reader 350 so as to perform the reading of the barcode by the barcode reader 350 with respect to the first reagent container rack 310 or the second reagent container rack 320 arranged with the replaced reagent. Specifically, in reading the barcodes 300a, 321b to 326b, or 321c to 326c of the second reagent container rack 320 and the reagent container 300 held in the second reagent container rack 320, the barcode 321b for identifying the positional information (holder number) is first read while rotating the second reagent table 12 in the direction of the arrow G (counterclockwise direction) in FIG. 5. Subsequently, the barcode 300a for identifying the detailed identifying information or the barcode 321c for identifying the no-container information are read, and thereafter, the barcode 322b representing the positional information is read. Thus, the positional information (holder number) (barcodes 321b to 326b) and the detailed identifying information (barcode 300a) or the no-container information (barcodes 321c to 326c) corresponding to the positional information are alternately read. The detailed identifying information includes container type information, reagent ID, and lot number.

In reading the barcodes 300a, 311b to 312b, or 311c to 312c of the first reagent container rack 310 and the reagent container 300 held in the first reagent container rack 310, the second reagent table 12 is first rotatably moved until reaching the position at where the gap 12a (see FIG. 5) of the second reagent table 12 faces the barcode reader 350. Thereafter, similar to when reading the barcode 300a of the second reagent container rack 320 described above and the reagent container 300 held in the second reagent container rack 320, the barcode reader 350 alternately reads the positional information (holder number) (barcodes 311b to 312b) and the detailed identifying information (barcode 300a) or the no-container information (barcodes 311c to 312c) corresponding to the positional information through the gap 12a (see FIG. 5) while the first reagent table 11 is being rotated in the direction of the arrow G (counterclockwise direction) of FIG. 5. The read positional information and the detailed identifying information or the no-container information corresponding to the positional information (holder number) are transmitted to the control section 501 and stored in the RAM 501*c*.

In step S48, the barcode read information stored in the RAM 501*c* is transmitted to the control section 4*a* by the control section 501.

When the barcode read information is transmitted from the control section 501 to the control section 4*a*, judgment is made on whether or not the barcode read information is received by the control section 4*a* in step S34 shown in FIG. 19. If judged that the barcode read information is received in step S34, the barcode read information is stored in the hard disc 401*d* in step S35, and the process proceeds to step S36. In step S36, the detailed information such as reagent name, type of container, lot number, and expiration date for all the reagents in the reagent rack holding the replaced reagent are acquired with reference to the reagent master, the reagent lot master, and the container master described above based on the barcode read information ((positional information) holder number, reagent ID, and container type information) stored in the hard disc 401*d* by the control section 4*a*. In step S36, the detailed information such as positional information, acquired reagent name, type of container, lot number, and expiration date are reflected on the first reagent mark 421, second reagent mark 422 or reagent non-arranged mark 427 and the reagent detailed displaying region 430 of the reagent managing screen 410 by the control part 4*a* (see FIG. 10). Since the remaining amount of the replaced reagent is unknown, the remaining amount indicator is displayed in a predetermined color (gray).

Figure 21:
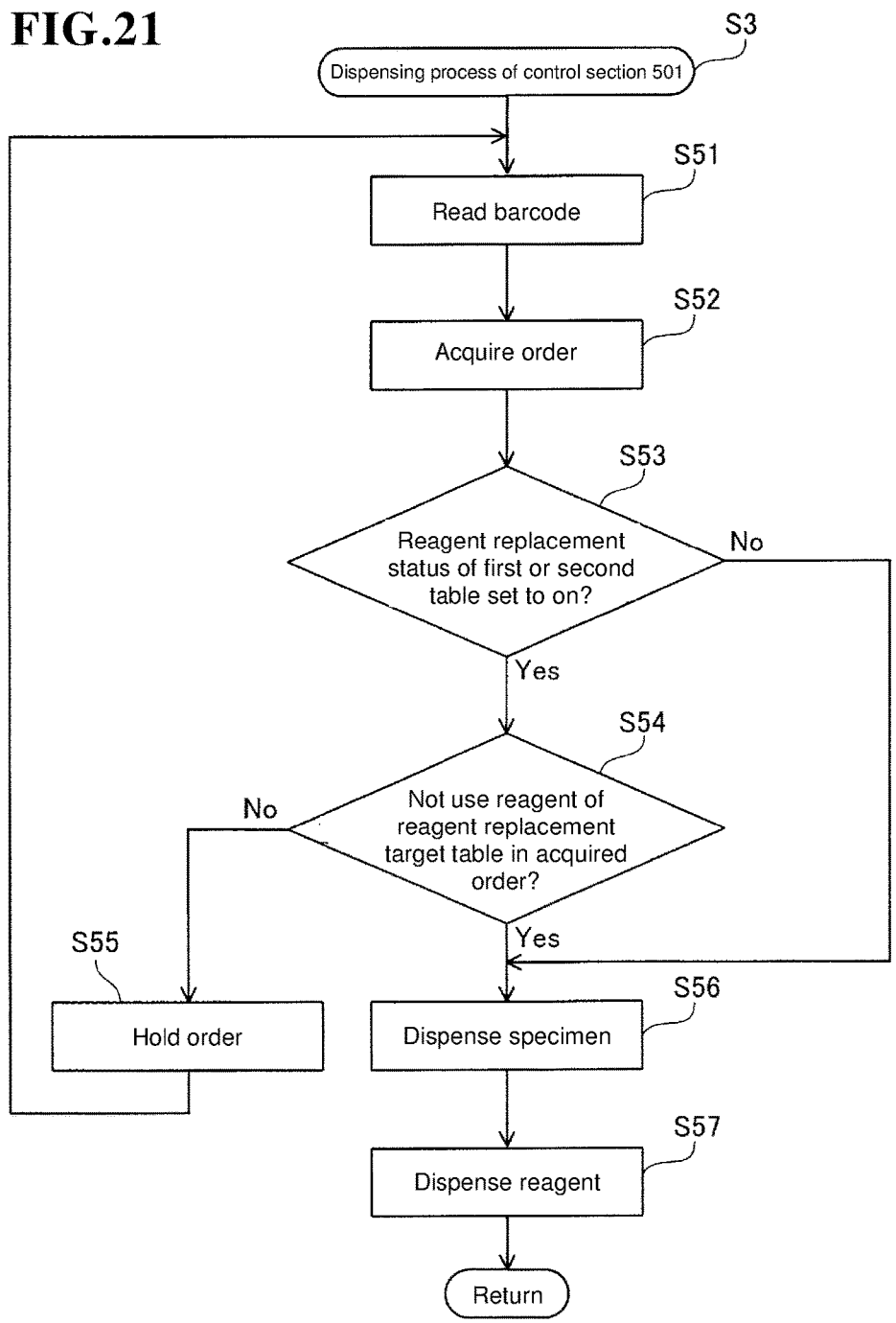
FIG. 21 is a flowchart for describing the dispensing process by the control section of the measurement mechanism unit of the sample analyzer according to the one embodiment of the present invention.

FIG. 21 is a flowchart for describing the details of the dispensing process of the control section 501 executed in step S3 of the flowchart shown in FIG. 27. The dispensing process flow the control section 501 of the sample analyzer 1 according to the present embodiment will now be described with reference to FIGS. 3, 5, and 21.

First, in step S51 shown in FIG. 21, the barcode attached to the test tube 250 accommodating the specimen conveyed by the conveyance mechanism unit 3 is read by controlling the barcode reader 3*c* by the control section 501. In step S52, the order is acquired based on the read barcode information by the control section 501, and the process proceeds to step S53. In step S53, judgment is made on whether or not the reagent replacement status of the first reagent table 11 or the second reagent table 12 is set to ON by the control section 501. This process is performed by the control section 501 checking the status register incorporated in the drive circuit of the reagent replacement target table. If judged that one of the reagent replacement statuses of the first reagent table 11 and the second reagent table 12 is set to ON in step S53, the process proceeds to step S54. If judged that neither reagent replacement status is set to ON in step S53, the process proceeds to step S56. The order will be described below. The order is information containing analyzing items associated with the information for specifying the specimen. The order is registered in a host computer (not shown) connected to the control device 4 or stored in the control device 4 by being manually input by the user. After acquiring the barcode information of the specimen, the control device 4 searches for the corresponding order from the order stored inside or acquires the order by inquiring the host computer with the specimen ID as the key. The order acquired by the control device 4 is transmitted from the control section 4*a* of the control device 4 to the control section 501 of the measurement mechanism unit 2, so that the control section 501 acquires the order.

Figure 23:
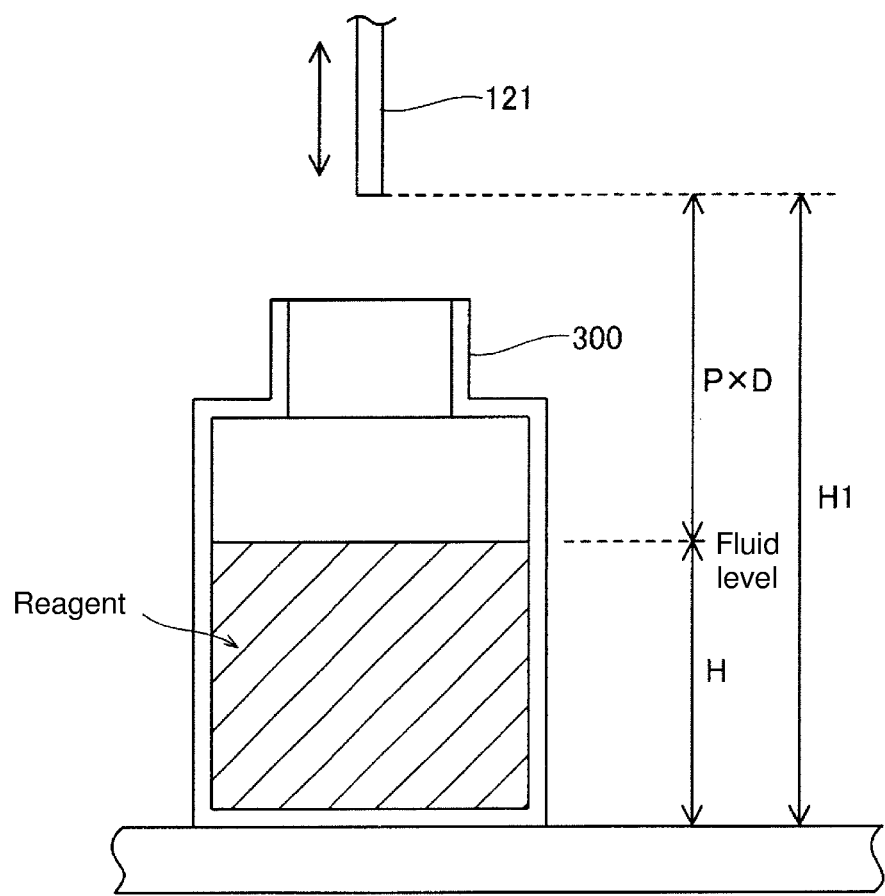
FIG. 23 is a conceptual view for describing a method of calculating the remaining amount of the reagent.

In step S56, the specimen dispensing driving section 70*a* is controlled according to the order by the control section 501, the specimen accommodated in the test tube 250 conveyed by the conveyance mechanism unit 3 is suctioned by the specimen dispensing arm 70, and the suctioned specimen is dispensed into the cuvette 200 held at the cuvette holding part 62 of the cuvette conveying table 61. In step S57, the reagent dispensing driving section 70*a* is controlled by the control section 501, and suction of the reagent is carried out through the holes 22*a*, 22*b*, or 22*c* (see FIG. 3) of the outer wall part 20 of the reagent storing section 6 by the reagent dispensing arm 120, and the suctioned reagent is dispensed into the cuvette 200 completed with warming. As shown in FIG. 23, in step S57, the pipette part 121 of the reagent dispensing arm 120 moves below the initial position (height H1) for suctioning the reagent. The pipette part 121 is driven by the stepping motor, and moves by a movement distance D every time one pulse is input to the stepping motor. The fluid level of the reagent is detected by the sensor arranged at the distal end of the pipette part 121 thereon. The number of pulse P, which is one of the fluid level detection information of when the sensor detects the fluid level of the reagent, is acquired.

If judged that one of the reagent replacement status of the first reagent table 11 and the second reagent table 12 is set to ON by the control section 501 in step S53, judgment is made on whether or not the reagent analyzing item specified by the acquired order uses the reagent of the reagent replacement target table in step S54. If judged that the reagent analyzing item specified by the acquired order does not use the reagent of the reagent replacement target table in step S54, the process proceeds to steps S56 and S57, and the processes described above are performed. Furthermore, if judged that the analyzing item specified by the acquired order uses the reagent of the reagent replacement target table, the acquired order is held in step S55. The steps S51 to S55 are repeated until judged that the reagent analyzing item specified by the acquired order does not use the reagent of the reagent replacement target table. Regarding the held order, if judged that the reagent analyzing item specified by the acquired order does not use the reagent of the reagent replacement target table, the processes of step S56 and S57 are executed in order.

The reagent is replaced as described above in the present embodiment.

In the above description, a case of replacing the reagent has been described, but when adding the reagent, specification of the reagent non-arranged mark 427 corresponding to the holding part 311, 312 or 321 to 326 arranged with the reagent to be added is carried out in step S21 shown in FIG. 27. The details of specifying the reagent displaying region when adding the reagent will be described below. That is, the user checks the arrangement of the reagent by the reagent arrangement displaying region 420 of the reagent managing screen 410 shown in FIG. 7. The user specifies by touching directly by hand the reagent non-arranged mark 427 corresponding to the holding part of the reagent container rack that holds the reagent to be added from the reagent non-arranged mark 427 (e.g., "A14-1", "B14-2", etc., of FIG. 7). In step S21, when the user pushes the replacement/addition button 440*a* with the reagent non-arranged mark 427 specified, the instruction to add the reagent to be added is completed. Thereafter, the reagent is added through operations similar to steps S31 to S37 shown in FIG. 19, steps S41 to S48 shown in FIG. 20, and steps S51 to S57 shown in FIG. 21.

Figure 22:
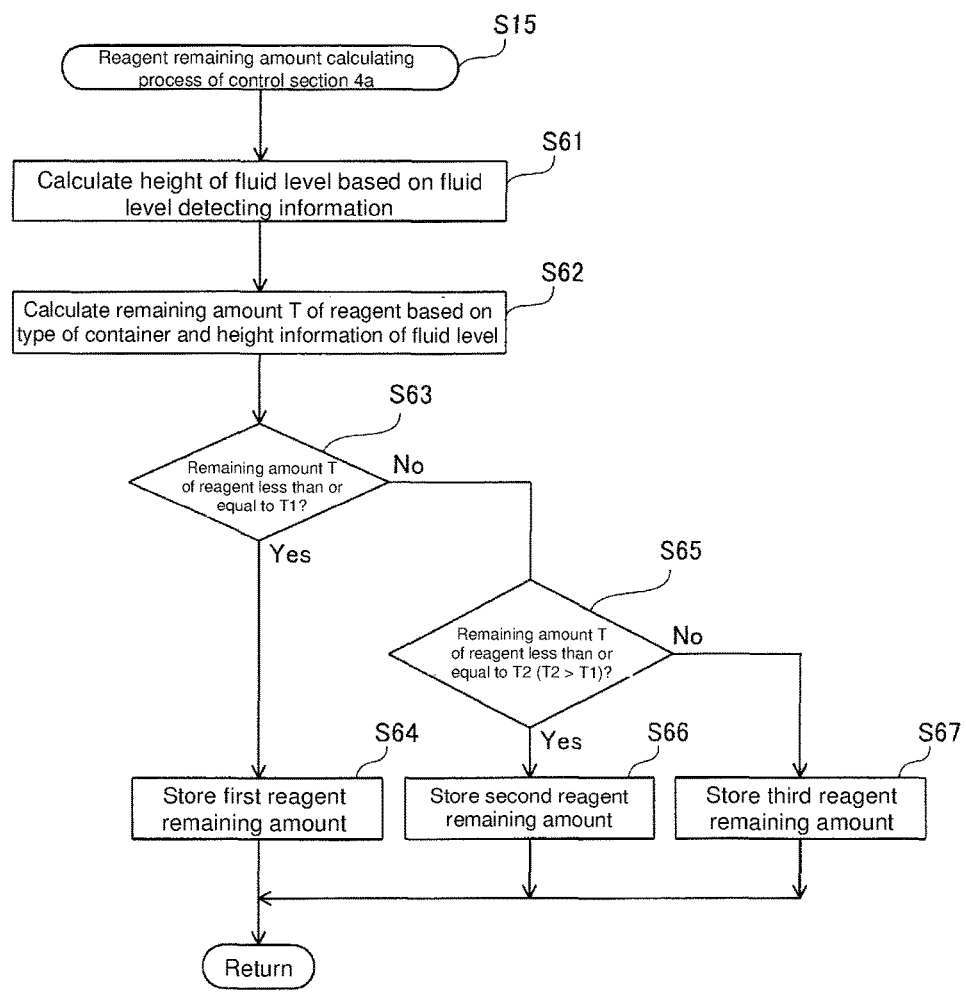
FIG. 22 is a flowchart for describing the process of displaying the remaining amount of the reagent in the reagent managing screen of the sample analyzer according to the one embodiment of the present invention.
Figure 24:
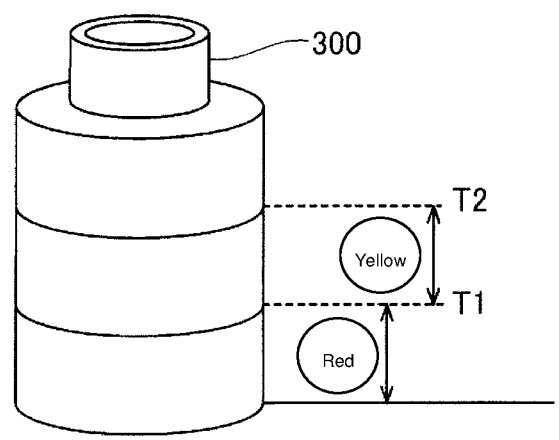
FIG. 24 is a conceptual view for describing the correspondence relationship between the remaining amount of the reagent and the color of the remaining amount indicator.

FIG. 22 is a flowchart for describing the details of the reagent remaining amount calculating process of the control section 4*a* executed in step S15 of the flowchart shown in FIG. 27. FIG. 23 is a view for describing the method of calculating the remaining amount of the reagent. FIG. 24 is a view for describing the correspondence relationship between the remaining amount of the reagent and the color of the remaining amount indicator. The process of calculating the remaining amount in the remaining amount indicator of the reagent mark will now be described with reference to FIGS. 10 and 22 to 24.

First, in step S61 shown in FIG. 22, the height of the fluid level is calculated based on the received fluid level detection information by the control section 4a. The fluid level detection information contains number of pulses P and distance D of when the fluid level described above is detected. The reagent container is specified based on the container ID with reference to the container master, and the inner area S in the horizontal direction of the specified reagent container is acquired by the control section 4a. Furthermore, the reagent name is acquired based on the reagent ID with reference to the reagent master. The height H of the fluid level is obtained by the following equation (1) by the control section 4a.

$$H \text{ (Height of fluid level)} = H1 \text{ (height of initial position)} - P \text{ (number of pulses)} \times D \text{ (movement distance of one pulse)} \quad (1)$$

In step S62, the remaining amount T of the reagent is calculated by the following equation (2) by the control section 4a from the acquired inner area S of the reagent container and the acquired height H of the fluid level of the reagent.

$$T \text{ (remaining amount)} = H \text{ (height of fluid level)} \times S \text{ (inner area of reagent container)} \quad (2)$$

In step S63, judgment is made on whether or not the remaining amount T of the reagent is less than or equal to the measurement canceling remaining amount T1. As shown in FIG. 24, when the remaining amount T of the reagent is less than or equal to the measurement canceling remaining amount T1, the first reagent remaining amount indicating that there is not remaining amount of the reagent is stored in the hard disc 401d in step S64. If the remaining amount T of the reagent is greater than the measurement canceling remaining amount T1, determination is made on whether or not the remaining amount T of the reagent is less than or equal to a warning remaining amount T2 in step S65.

As shown in FIG. 24, if the remaining amount T of the reagent is less than or equal to the warning remaining amount T2, the second reagent remaining amount indicating that the remaining amount of the reagent is few is stored in the hard disc 401d in step S66. If the remaining amount T of the reagent is greater than the warning remaining amount T2, the third reagent remaining amount indicating that the remaining amount of the reagent is sufficient is stored in the hard disc 401d in step S67.

The steps S61 to S67 are repeated every time measurement is performed. As described above, the remaining amount indicator is displayed in red for the first reagent remaining amount, the remaining amount indicator is displayed in yellow for the second reagent remaining amount, and the remaining amount indicator is not displayed for the third reagent remaining amount. Therefore, the user can easily recognize the remaining amount of the reagent by color displaying the reagent remaining amount in the remaining amount indicator based on the calculated reagent remaining amount.

Figure 25:
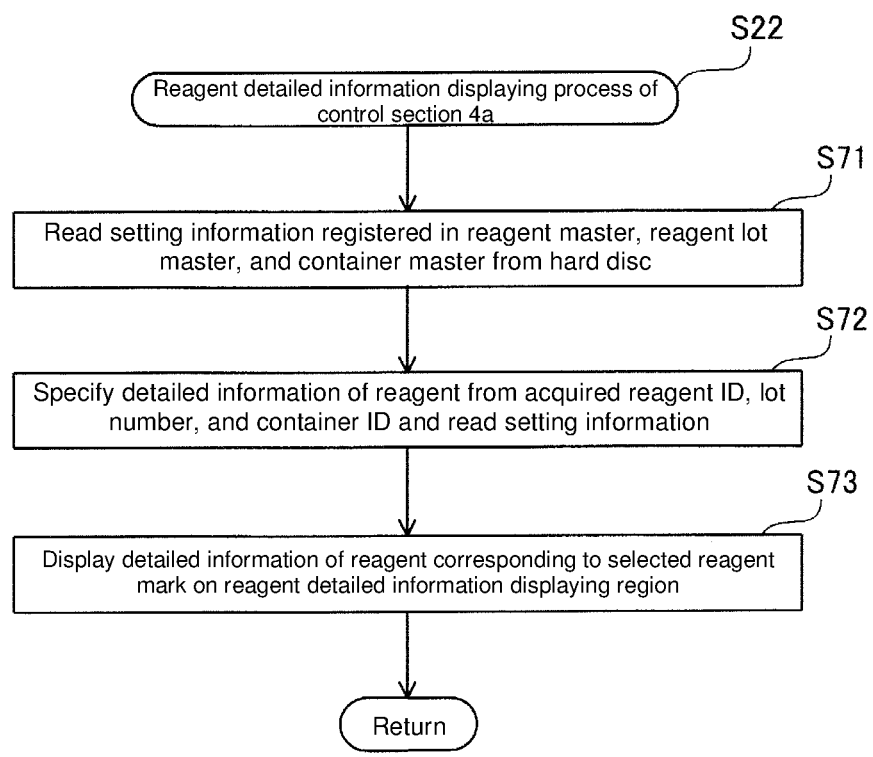
FIG. 25 is a flowchart for describing the process of displaying the detailed information of the reagent on the reagent detailed information displaying region.

FIG. 25 is a flowchart for describing the details of the reagent detailed information displaying process of the control section 4a executed in step S22 of the flowchart shown in FIG. 27. The process flow of displaying the detailed information of the reagent on the reagent detailed information displaying region will now be described with reference to FIG. 25.

First, in step S71, the reagent setting information, reagent lot setting information, and container setting information respectively registered in the reagent master, the reagent lot master, and the container master are read from the hard disc 401d by the control section 4a.

In step S72, "holder number", "reagent name", "necessity of stirring", "reagent lot number", "expiration date", and "type of container" are specified based on the barcode read information stored in the hard disc 401d by the control section 4a. Specifically, the "holder number" is specified from the positional information of the barcode of the reagent container rack. The reagent ID and the reagent setting information are checked, and "reagent name" and "necessity of stirring" are specified. The reagent lot number and the reagent lot setting information are checked, and "reagent lot number" and "expiration date" are specified. The container ID and the container setting information are checked, and "type of container" is specified. Regarding the reagents used in the measurement, the remaining amount of the reagent is calculated in the above manner, and thus "usable amount" and "remaining number of tests" are specified from the calculated remaining amount of the reagent. If the reagent is not used even once in the measurement after being replaced, "usable amount" and "remaining number of tests" are not calculated. Furthermore, "set date" and "set time" are specified by the date and time at when reading of the barcode was performed. The barcode read information is acquired in replacement or addition of the reagent, and stored in the hard disc 401d.

In step S73, the detailed information specified in the above-described step S72 is displayed on the reagent detailed information displaying region. If the reagent is not used even once in the measurement after being replaced, "usable amount" and "remaining number of tests" are not displayed.

Figure 26:
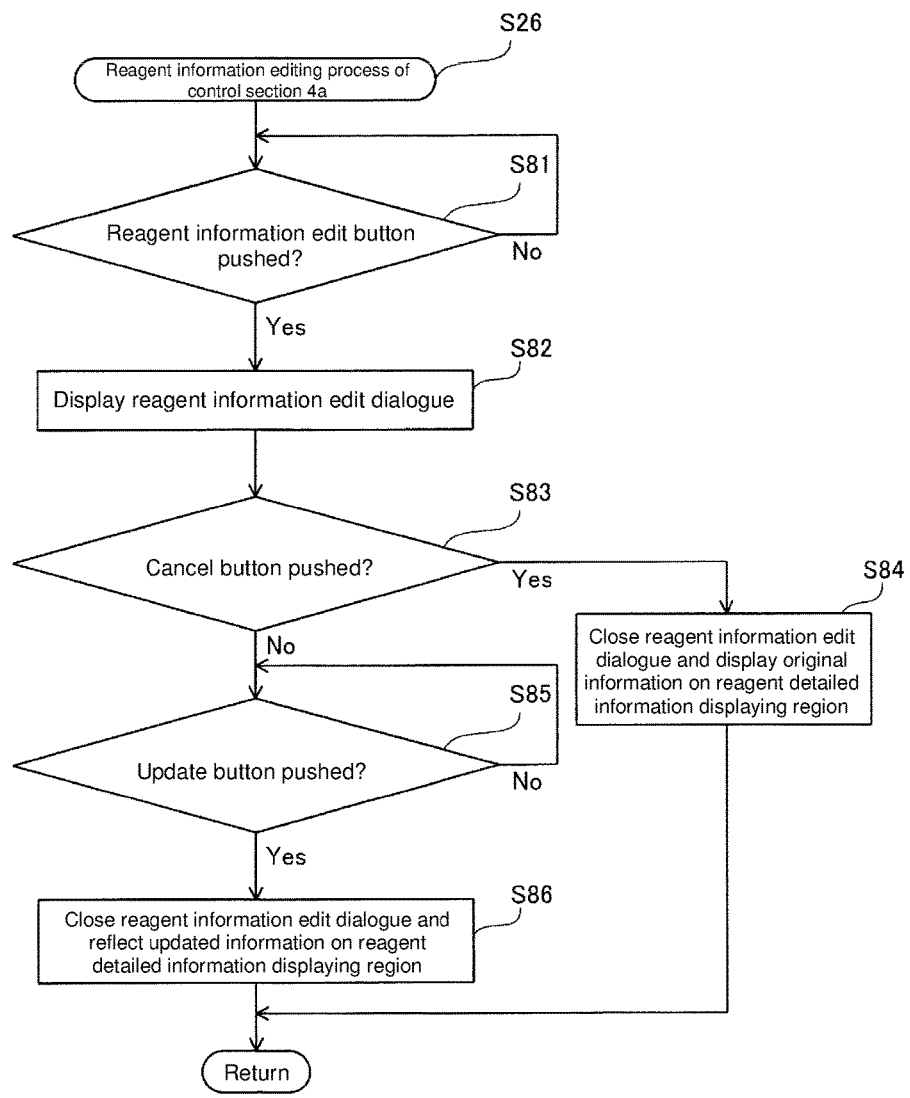
FIG. 26 is a flowchart for describing the process of editing the detailed information of the reagent displayed on the reagent detailed information displaying region.

FIG. 26 is a flowchart for describing the details of the reagent information editing process of the control section 4a executed in step S26 of the flowchart shown in FIG. 27. The process flow of editing the detailed information displayed on the reagent detailed information displaying region will now be described with reference to FIGS. 11 and 26.

First, in step S81, judgment is made on whether or not the reagent information edit button 440b is pushed. If the reagent information edit button 440b is not pushed, the relevant judgment is repeated. If the reagent edit button 440b is pushed, the reagent information edit dialogue 450 is displayed on the display device 4b in step S82, as shown in FIG. 11. The user edits the detailed information in the reagent information edit dialogue 450.

In step S83, judgment is made on whether or not the cancel button 453 is pushed by the control section 4a. If the cancel button 453 is pushed, the reagent information edit dialogue 450 is closed and the original detailed information is displayed on the reagent detailed information displaying region 430 in step S84. If the cancel button 453 is not pushed, judgment is made on whether or not the update button 452 is pushed in step S85. If the update button 452 is not pushed, the relevant judgment is repeated. If the update button 452 is pushed, the reagent information edit dialogue 450 is closed and the edited detailed information is reflected on the reagent information displaying region 430 in step S86.

In the present embodiment, only the detailed information of the reagent corresponding to the specified reagent mark can be displayed on the reagent detailed information displaying region 430 by specifying the reagent mark displayed on the reagent arrangement displaying region 420, as described above. Thus the reagent detailed information displaying region 430 does not need to be arranged for the number of reagents, and thus percentage of the reagent detailed information displaying region 430 occupying the reagent managing screen 410 is set to a constant size. Therefore, when arranging a great number of reagents, the detailed information of the reagent arranged in the reagent storing section 6 can be easily displayed.

Furthermore, in the present embodiment, the user is able to check the arrangement of the reagent accommodated in a plurality of reagent container racks with the display device 4b by displaying the rack mark and each reagent mark in correspondence to the arrangement state of each reagent accommodated in the plurality of reagent container racks, as described above. The user then can easily manage the reagents.

Moreover, in the present embodiment, the user is able to easily distinguish the current specified reagent from the reagents other than the specified reagent by displaying the background with respect to the reagent name of the reagent name displaying part of the specified reagent mark in blue, and displaying the background with respect to the reagent name of the reagent name displaying part of the non-specified reagent mark in white in the reagent arrangement displaying region 420, as described above.

In the present embodiment, the user recognizes by warning display on the display device 4b that the remaining amount T of the reagent is less than or equal to the measurement canceling remaining amount T1 or the warning remaining amount T2 by displaying a warning that the remaining amount T of the reagent is less than or equal to the measurement canceling remaining amount T1 or the warning remaining amount T2 on the reagent mark corresponding to the reagent when the remaining amount T becomes less than or equal to the measurement canceling remaining amount T1 or the warning remaining amount T12, as described above.

In the present embodiment, the user can recognize the difference in the remaining amount of the reagents by difference in color by displaying the remaining indicator in a predetermined color (e.g., red) when the remaining amount T of the reagent becomes less than or equal to the measurement canceling remaining amount T1, and displaying the remaining amount indicator in a predetermined color (e.g., yellow) when the remaining amount of the reagent becomes the warning remaining amount T2, as described above.

Moreover, the user is able to accurately know at which accommodating position of which reagent container rack the reagent is arranged by displaying the positional information (holder number) of the reagent read from the barcode on the reagent mark, as described above.

In the present embodiment, the lot number and the expiration date of the reagent corresponding to the specified reagent mark can be recognized on the reagent detailed information displaying region 430 by specifying the reagent mark in the reagent arrangement displaying region 420, as described above. The user thus can judge the replacement timing, etc., of the reagent.

In the present embodiment, the remaining number of tests, the set date, and the set time of the reagent corresponding to the specified reagent mark can be checked on the reagent detailed information displaying region by specifying the reagent mark in the reagent arrangement displaying region 420, as described above. The user then can judge the replacement timing, etc., of the reagent.

In the present embodiment, the user can easily recognize the arrangement of the reagent by configuring the first reagent table 11 and the second reagent table 12 such that each reagent can be arranged in an annular form, and displaying the reagent mark in an annular form in correspondence to the annular arrangement of the reagent in the first reagent table 11 and the second reagent table on the reagent arrangement displaying region 420, as described above.

In the present embodiment, after specifying the reagent in the reagent arrangement displaying region 420 of the reagent managing screen 410, the reagent can be replaced with the replacement/addition button 440a in the reagent managing screen 410, as described above. The user then can easily replace the reagent.

In the present embodiment, the detailed information of the reagent displayed on the reagent detailed information displaying region 430 of the reagent managing screen 410 can be edited with the reagent information edit button 440b displayed on the operation means displaying region 440 of the same reagent managing screen 410, as described above. The convenience of the user thus enhances.

In the present embodiment, the user can easily edit the detailed information of the reagent with the reagent information edit dialogue 450 displayed by pushing the reagent information edit button 440b, as described above.

In the present embodiment, the rack mark including the specified reagent mark is displayed in a predetermined color (e.g., green) in a retrievable state in which the user can retrieve the reagent arranged in the first table 11 or the second reagent table 12 when replacing the reagent, as described above. The rack mark including the specified reagent mark is displayed in a predetermined color (e.g., yellow) in a waiting state from when the replacement/addition button 440a is pushed until the retrievable state is obtained. The user can judge the retrievable state and the waiting state from the reagent managing screen 410 of the display device 4b, and thus can easily replace the reagent.

In the present embodiment, the reagent can be added to the portion not arranged with the reagent of the reagent arranging section by specifying the reagent non-arranged mark and pushing the replacement/addition button, as described above.

In the present embodiment, the mistaken arrangement mark B is displayed for the corresponding reagent mark if the reagent that requires stirring is arranged at a position where stirring cannot be performed in the reagent managing screen 410, as described above. The expired mark C is displayed for the reagent mark corresponding to the expired reagent. The stable time-out mark D is displayed for the reagent mark of the reagent that has elapsed a predetermined time (e.g., eight hours) from the set date and set time of the reagent. The user thus can check the reagent that has a problem to be used for analysis from the reagent managing screen 410. The managing of the reagent such as replacing the reagent that has a problem to be used for analysis with a new reagent is thus easily carried out.

The embodiments disclosed herein are illustrative and should not be construed as being restrictive. The scope of the invention is defined by the appended claims rather than by the description of the embodiments, and all changes that fall within meets and bounds of the claims, or equivalence of such meets and bounds are therefore intended to be embraced by the claims.

For instance, an example of displaying the positional information (holder number), reagent name, and remaining amount indicator on the reagent mark has been described in the above embodiments, but the present invention is not limited thereto, and only the reagent name may be displayed.

An example of distinguishing the specified reagent mark from the other reagent marks by changing the color of the specified reagent mark has been described in the above embodiments, but the present invention is not limited thereto, and the shape or size of the specified reagent mark may be changed.

An example of displaying a warning of the remaining amount of the reagent with the remaining amount indicator when the remaining amount of the reagent becomes small has been described in the above embodiments, but the present invention is not limited thereto, and the remaining amount indicator may be displayed even if the remaining amount of the reagent is suffice.

An example of displaying the color of the remaining amount indicator in yellow when the remaining amount T of the reagent is less than or equal to the warning remaining amount T2 and displaying in red when less than or equal to the measurement canceling remaining amount T1 has been described in the above embodiments, but the present invention is not limited thereto, and may be displayed in colors other than yellow and red. In addition to changing the color of the remaining amount indicator by the remaining amount of the reagent, the shape, pattern, and the like of the remaining amount indicator may be changed.

An example of displaying the reagent name on the reagent name displaying part of the reagent mark has been described in the above embodiments, but the present invention is not limited thereto, and the reagent name may be displayed in the vicinity of the reagent mark.

An example of displaying as a mark an icon of a combination of character and figure on the display device so as to be specifiable has been described in the above embodiments, but the present invention is not limited thereto, and a button may be displayed on the display device as the mark. For instance, a button configured only from a rectangle with a character inside may be used.

An example of providing a touch panel function to the display device, so that the user can directly touch button etc. displayed on the reagent managing screen for selection or operation has been described in the above embodiments, but the present invention is not limited thereto, and selection or operation may be carried out by specifying button etc. displayed on the reagent managing screen with keyboard or mouse.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A sample analyzer comprising:
a reagent arranging section for arranging a plurality of reagents in annular form and rotatably;
an analyzing section for analyzing a measurement sample prepared by mixing a sample and the reagent arranged on the reagent arranging section;
a touch panel; and
a display control section that concurrently displays, on the touch panel, a reagent arrangement displaying region, a reagent detailed information displaying region, and an operation displaying region;
wherein the reagent arrangement displaying region includes a plurality of reagent marks, each inscribed with a reagent name of a reagent, wherein the reagent marks are displayed in annular form corresponding to an arrangement of the reagents, respectively, on the reagent arranging section and are displayed in a manner selectable with the touch panel;
wherein the reagent detailed information displaying region includes detailed information related to the reagent corresponding to the reagent mark selected with the touch panel on the touch panel,
wherein the operation displaying region includes a replacement instructing button for replacing the reagent corresponding to the reagent mark selected with the touch panel on the touch panel.

2. The sample analyzer according to claim 1, wherein the display control section controls the touch panel to display the selected reagent mark in a manner distinguishable from reagent marks other than the selected reagent mark on the reagent arrangement displaying region.

3. The sample analyzer according to claim 1, wherein the display control section controls the touch panel to display the reagent mark in a manner that remaining amount of the reagent is identifiable.

4. The sample analyzer according to claim 1, wherein the detailed information comprises a reagent name, usage order, and remaining amount.

5. The sample analyzer according to claim 1, wherein the display control section controls the touch panel to display positional information indicating an accommodating position of the reagent on the reagent arranging section, wherein the reagent mark is displayed so as to correspond to the positional information of the reagent on the reagent arranging section.

6. The sample analyzer according to claim 1, wherein the display control section controls the touch panel to display reagent lot information indicating lot number of the reagent corresponding to the selected reagent mark and reagent expiration date information indicating expiration date of the reagent corresponding to the selected reagent mark on the reagent detailed information displaying region.

7. The sample analyzer according to claim 1, wherein the display control section controls the display device to display reagent remaining test information indicating remaining number of tests of the reagent corresponding to the selected reagent mark on the reagent detailed information displaying region.

8. The sample analyzer according to claim 1, wherein the operation displaying region includes a reagent information edit button for editing the detailed information of the reagent corresponding to the selected reagent mark is displayed in a manner selectable by the touch panel on the touch panel.

9. The sample analyzer according to claim 8, wherein when the reagent marks is selected by the touch panel and the reagent information edit button is selected by the touch panel, the display control section controls the touch panel to display an editing screen for editing the detailed information of the reagent corresponding to the selected reagent mark.

10. The sample analyzer according to claim 1, wherein the display control section controls the touch panel to display a reagent non-arranged mark in a manner distinguishable from the reagent mark on the reagent arrangement displaying region, the non-arranged mark corresponds to a portion not arranged with the reagent of the reagent arranging section; and wherein when the non-arranged marks is selected by the touch panel and the replacement instructing button is selected by touch panel, the reagent arranging section performs a reagent adding operation for adding a reagent to the portion of the reagent arranging section corresponding to the selected non-arranged mark.

11. The sample analyzer according to claim 1, wherein the detailed information comprises necessity of stirring.

12. A sample analyzer comprising:
a reagent arranging section for arranging a plurality of reagents in annular form and rotatably;
an analyzing section for analyzing a measurement sample prepared by mixing a sample and the reagent arranged on the reagent arranging section;
a touch panel; and
a display control section for displaying a reagent managing screen that includes a first region for displaying a plurality of reagent marks, each inscribed with one of a plurality of reagent names, wherein each of the reagent names displays a name of a particular reagent, wherein the plurality of reagent marks are arranged in annular form to correspond with arrangement of the reagents, respectively, on the reagent arranging section, the reagent managing screen including a second region for displaying a replacement mark for replacing the reagent arranged on the reagent arranging section, further wherein each reagent mark and replacement mark are displayed in a manner selectable by the touch panel; and
a controller configured to:
receive a selection of one of the reagent marks from the touch panel; and
perform, with the reagent arranging section, a replacement operation that replaces the reagent corresponding to the selected reagent mark.

13. The sample analyzer according to claim 12, wherein the reagent managing screen further includes a third region for displaying detailed information of the reagent corresponding to the selected reagent mark.

14. The sample analyzer according to claim 13, wherein an edit mark for editing the detailed information of the reagent corresponding to the selected reagent mark is displayed in a manner selectable by the touch panel on the second region.

15. The sample analyzer according to claim 14, wherein when the reagent marks is selected by the touch panel and the edit mark is selected by the touch panel, the display control section controls the touch panel to display an editing screen for editing the detailed information of the reagent corresponding to the selected reagent mark.

16. The sample analyzer according to claim 12, wherein the display control section controls the touch panel to display a reagent non-arranged mark in a manner distinguishable from the reagent mark on the first region, the non-arranged mark corresponds to a portion not arranged with the reagent of the reagent arranging section; and
wherein when the non-arranged marks is selected by the touch panel and the replacement mark is selected by the touch panel, the reagent arranging section performs a reagent adding operation for adding a reagent to the portion of the reagent arranging section corresponding to the selected non-arranged mark.

17. The sample analyzer according to claim 12, wherein the detailed information comprises necessity of stirring.

18. A sample analyzer comprising:
a reagent arranging section for arranging a plurality of reagents in annular form and rotatably;
an analyzing section for analyzing a measurement sample prepared by mixing a sample and the reagent arranged on the reagent arranging section;
a touch panel; and
a display control section that concurrently displays, on the touch panel, a reagent arrangement displaying region, a reagent detailed information displaying region, and an operation displaying region;
wherein the reagent arrangement displaying region includes a plurality of reagent marks, each inscribed with a reagent name of a reagent, wherein the reagent marks are displayed in annular form corresponding to an arrangement of the reagents, respectively, on the reagent arranging section and are displayed in a manner selectable with the touch panel;
wherein the reagent detailed information displaying region includes detailed information related to the reagent corresponding to the reagent mark selected with the touch panel on the touch panel,
wherein the operation displaying region includes a reagent information edit button for editing the detailed information of the reagent corresponding to the selected reagent mark is displayed in a manner selectable by the touch panel on the touch panel.

19. The sample analyzer according to claim 18, wherein when the reagent marks is selected by the touch panel and the reagent information edit button is selected by the touch panel, the display control section controls the touch panel to display an editing screen for editing the detailed information of the reagent corresponding to the selected reagent mark.

20. The sample analyzer according to claim 18, wherein the detailed information comprises necessity of stirring.

* * * * *